(12) United States Patent
Muraguchi et al.

(10) Patent No.: US 8,445,193 B2
(45) Date of Patent: May 21, 2013

(54) MICROWELL ARRAY CHIP FOR DETECTING ANTIGEN-SPECIFIC LYMPHOCYTES, METHOD OF DETECTING AND METHOD OF MANUFACTURING ANTIGEN-SPECIFIC LYMPHOCYTES, AND METHOD OF CLONING ANTIGEN-SPECIFIC LYMPHOCYTE ANTIGEN RECEPTOR GENES

(75) Inventors: Atsushi Muraguchi, Toyama (JP); Hiroyuki Kishi, Toyama (JP); Eiichi Tamiya, Kanazawa (JP); Masayasu Suzuki, Toyama (JP)

(73) Assignee: Vivalis, Roussay (FR)

( * ) Notice: Subject to any disclaimer, the term of this patent is extended or adjusted under 35 U.S.C. 154(b) by 443 days.

(21) Appl. No.: 12/337,481

(22) Filed: Dec. 17, 2008

(65) Prior Publication Data
US 2009/0181859 A1 Jul. 16, 2009

Related U.S. Application Data

(62) Division of application No. 10/534,800, filed as application No. PCT/JP03/12500 on Sep. 30, 2003, now abandoned.

(30) Foreign Application Priority Data

Nov. 14, 2002 (JP) ................................ 2002-331031
Nov. 29, 2002 (JP) ................................ 2002-346728

(51) Int. Cl.
*G01N 33/53* (2006.01)
*C12N 5/06* (2006.01)
*C12N 5/08* (2006.01)
*C12N 5/00* (2006.01)

(52) U.S. Cl.
USPC ............. 435/6; 435/326; 435/372.2; 435/377

(58) Field of Classification Search ........................ None
See application file for complete search history.

(56) References Cited

U.S. PATENT DOCUMENTS

| | | | |
|---|---|---|---|
| 4,729,949 A | 3/1988 | Weinreb et al. | |
| 5,272,081 A | 12/1993 | Weinreb et al. | |
| 5,310,674 A | 5/1994 | Weinreb et al. | |
| 5,506,141 A | 4/1996 | Weinreb et al. | |
| 6,087,103 A | 7/2000 | Burmer | |
| 6,210,910 B1 | 4/2001 | Walt et al. | |
| 6,232,066 B1 | 5/2001 | Felder et al. | |
| 6,377,721 B1 | 4/2002 | Walt et al. | |
| 6,410,252 B1 | 6/2002 | Lehmann et al. | |
| 6,548,263 B1 | 4/2003 | Kapur et al. | |
| 6,565,813 B1 | 5/2003 | Garyantes | |
| 2003/0027214 A1 | 2/2003 | Kamb | |
| 2003/0030184 A1 | 2/2003 | Kim et al. | |
| 2003/0064386 A1 | 4/2003 | Karaki et al. | |
| 2006/0078946 A1 | 4/2006 | Muraguchi et al. | |

FOREIGN PATENT DOCUMENTS

| | | |
|---|---|---|
| JP | 59-31685 A | 2/1984 |
| JP | 2001-504323 A | 4/2001 |
| JP | 2002-506200 A | 2/2002 |
| WO | WO-98/10284 A1 | 3/1998 |
| WO | WO 02/078844 A1 | 10/2002 |

OTHER PUBLICATIONS

Steenbakkers et al., J.Immunol.Method, 1992, v.152, pp. 69-77).*
EP Examination Report from Application No. 03 812 277.6, 2002.
J. Yano et al., Lymphocyte Function Detection Methods, 1994, pp. 262-267, Chugai Igaku Corp.
S. Ishida et al., Methods of Conducting Immunological Experiments I, II, 1995, pp. 742-747, published by Nankodo.
J.D. Altman et al., Science, vol. 274, Oct. 4, 1996, pp. 94-96.
H. Abts et al., Journal of Immunological Methods, vol. 125, 1989, pp. 19-28.
A.J. Roome et al., Experimental Biology, vol. 43, 1984, pp. 35-55.
D.A. Carson et al., Advances in Immunology, vol. 38, 1986, pp. 275-311.
J.S. Huston et al., Proc. Natl. Acad. Sci. USA, vol. 85, Aug. 1988, pp. 5879-5883.
Yamamura et al., Anal. Chem., vol. 77, pp. 8050-8056 (2005).
Biran, I., et al., "Optical Imaging Fiber-Based Single Live Cell Arrays: A High-Density Cell Assay Platform," Anal. Chem., vol. 74, pp. 3046-3054 (2002).
Tokimitsu, Y., et al., "Single Lymphocyte Analysis with a Microwell Array Chip," Cytometry Part A, pp. 1003-1010 (2007).
Abbas, A.K., et al., "Cellular and Molecular Immunology," Second Edition, W.B. Saunders Company, Philadelphia, PA, USA, pp. 92-93.
Chen, H.J.H., et al., "A novel micro-well array chip for liquid phase biomaterial processing and detection." Sensors and Actuators A, vol. 108, 2003, pp. 193-200.
Clark, E.A., et al., "Regulation of Human B-Cell Activation and Adhesion." Annu. Rev. Immunol., vol. 9, 1991. pp. 97-127.
Ostuni, E., et al., "Selective Deposition of Proteins and Cells in Arrays of Microwells," Langmuir, vol. 17, 2001 (Published on Web: Apr. 5, 2001), pp. 2828-2834.
Sredni, B., et al., "Antigen-Specific, Proliferating T Lymphocyte Clones. Methodology, Specificity, MHC Restricition and Alloreactivity," Immunological Rev., vol. 54, 1981, pp. 187-223.

* cited by examiner

*Primary Examiner* — Michail Belyavskyi
(74) *Attorney, Agent, or Firm* — Birch, Stewart, Kolasch & Birch, LLP

(57) ABSTRACT

A microwell array chip that has multiple microwells and is employed to contain a single lymphocyte specimen in each microwell and detect antigen-specific lymphocytes in single units; wherein the microwell array chip is of a shape and of dimensions where only one lymphocyte is contained in each microwell. A method of detecting antigen-specific lymphocytes comprising the steps of adding antigen to each microwell in the above microwell array chip, stimulating the lymphocyte specimen, and detecting lymphocyte specimens reacting with the antigen.

11 Claims, 10 Drawing Sheets

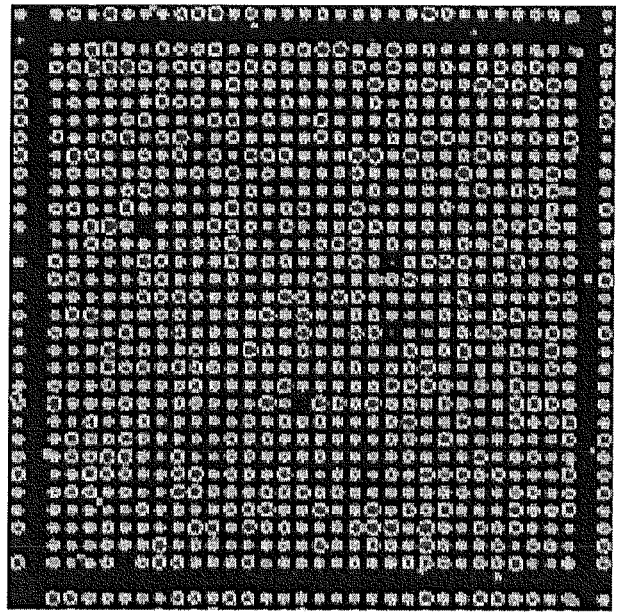
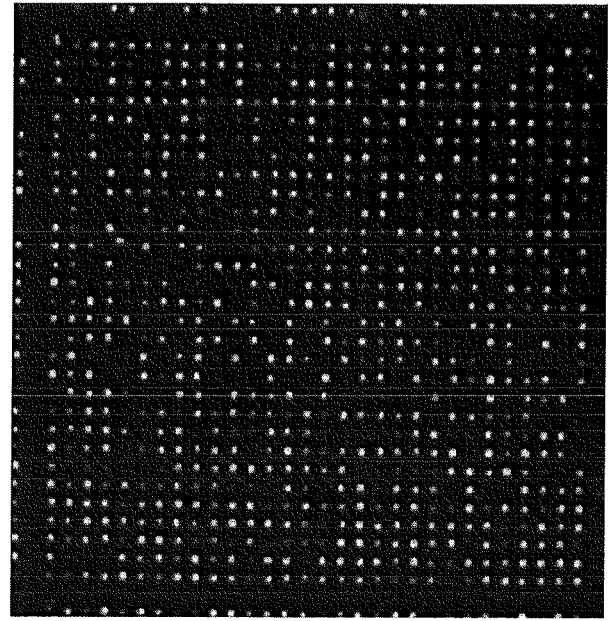
Fig 4

```
1st:   1 cagtctccagccaccctgtctttgtctccagggcaaagtagccaccctctcctgcnggg  60
            ||||||||||||||||||||| |||||||||||||||||||||||||||||||| |||
2nd:  55 cagtctccagccaccctgtctttgtctccagggg-aaag-agccaccctcctgcaggg 112

1st:  61 ccagtcagagtgttagcanctacttagcctggtaccaacagaaacactggccaggctccc 120
            |||||||||| ||||||| |||||||||||||||||||||||||||||||||||||||
2nd: 113 ccagtcagagtgttagcagctacttagcctggtaccaacagaaac-ctggccaggctccc 171

1st: 121 aggctcctnatctatgatgcatctcaacagggccactggccatcccagccaggttaagtgg 180
            |||||| |||||||||||||| ||||||||||||||||||||||||||||  |||||
2nd: 172 aggctcctcatctatgatgcatc-caacagggccactggccatcccagccaccttcagtgg 230

1st: 181 cagtgggtctgggacagacttcactctcaccatcancagcctagagcctgaagatttntgc 240
            |||||||||||||||||||||||||||||||||| ||||||||||||||||||||| ||
2nd: 231 cagtgggtctgggacagacttcactctcaccatcagcagcctagagcctgaagattttgc 290

1st: 241 agttnattactgtcancagcgtatcaactggcctctcactttcggcggagggaccaaggc 300
            ||| ||||||||||| ||||| ||||||||||||||||||||||||||||||||||||
2nd: 291 agttttattactgtcagcagcgtagcaactggcctcactttcggcgtcactttcggcggagggaccaagg- 349

1st: 301 tggagatcaaacgaactgtggctgcaccatctgtc 335
         |||||||||||||||||||||||||||||||||||
2nd: 350 tggagatcaaacgaactgtggctgcaccatctgtc 384
```

Fig 9

```
1st:   1 ggtcctgtctcaggtgcagctgcaggcagtcgggcccagtgactggtgaagccttcggag  60
         |||||||| ||||||||||||||||||| |||||||||| ||||||||||||||||||||
2nd:  48 ggtcctgtcccagctgcagctgcagg-agtcgggcccag-gactggtgaagccttcggag 105

1st:  61 accctgtccctcacctgcactgtctctggtggctccatcagcagtagtagttactactgg 120
         ||||||||||||||||||||||||||||||||||||||||||||||||||||||||||||
2nd: 106 accctgtccctcacctgcactgtctctggtggctccatcagcagtagtagttactactgg 165

1st: 121 ggctggatccgccagcccccagggaaggggctggagtggattgggagtatctattatagt 180
         |||||||||||||||||||||||||||||||||||||||||||||||||||||||||||
2nd: 166 ggctggatccgccagcccccagggaaggggctggagtggattgggagtatctattatagt 225

1st: 181 gggagcacctactacaacccgtccctcaagagtcgagtcaccatatccgtagacacgtcc 240
         ||||||||||||||||||||||||||||||| ||||||||||||||||||||||||||||
2nd: 226 gggagcacctactacaacccgtccctcaagagtcgagtcaccatatccgtagacacgtcc 285

1st: 241 aagaaccagttctccctgaagctgagctctgtgaccgccgcagacacggctgtgtattac 300
         ||||||||||||||||||||||||||||||||||||||||||||||||||||||||||||
2nd: 286 aagaaccagttctccctgaagctgagctctgtgaccgccgcagacacggctgtgtattac 345

1st: 301 tgtgcgagacag 312
         ||||||||||||
2nd: 346 tgtgcgagacag 357
```

MICROWELL ARRAY CHIP FOR DETECTING ANTIGEN-SPECIFIC LYMPHOCYTES, METHOD OF DETECTING AND METHOD OF MANUFACTURING ANTIGEN-SPECIFIC LYMPHOCYTES, AND METHOD OF CLONING ANTIGEN-SPECIFIC LYMPHOCYTE ANTIGEN RECEPTOR GENES

This application is a divisional application of U.S. patent application Ser. No. 10/534,800 filed Dec. 2, 2005 (abandoned), which is the National Phase of PCT/JP03/12500, filed Sep. 30, 2003, which claims priority to Japanese patent applications JP 2002-331031, filed Nov. 14, 2002, and JP 2002-346728 filed Nov. 29, 2002. The entire contents of all of the above are herein incorporated by reference.

A Sequence Listing is filed concurrently herewith as a text file "2009_03_13SeqListing.txt" via EFS-Web. Entry of the Sequence Listing into the present application is requested.

TECHNICAL FIELD

The present invention relates to a microwell array chip employed in detecting antigen-specific lymphocytes, a method of detecting antigen-specific lymphocytes, and a method of manufacturing antigen-specific lymphocytes. The present invention further relates to a method of cloning antigen-specific lymphocyte antigen receptor genes.

TECHNICAL BACKGROUND

In the past, antigen-specific lymphocytes have been detected by placing about 200,000 individual lymphocytes per well in a 96-well plate such as that shown in FIG. 3 and culturing them for from three days to a week ("Lymphocyte Function Detection Methods", ed. by Junichi Yano, Michio Fujiwara, Chugai Igaku Corp. (1994) (Nonpatent Reference 1) and "Methods of Conducting Immunological Experiments I, II", ed. by Shunsuke Ishida, Susumu Konda, Morosuke Moto, and Toshiyuki Hamaoka, Nankodo (1995) (Nonpatent Reference 2)).

These detection methods detect antigen-specific lymphocytes by:
1. Cell proliferation (uptake of $^3$H-thymidine, detection of live cells), and
2. Production of antibody and cytokine.

These methods are capable of determining the presence of antigen-specific lymphocytes in a lymphocyte population of about 200,000 cells. However, they are incapable of identifying individual antigen-specific lymphocytes present in the lymphocyte population.

By contrast, in recent years, a method of mixing antigen molecules labeled with fluorescent dye with lymphocytes to cause fluorescence-labeled antigen to bind to the antigen receptors of antigen-specific lymphocytes, and then using a flow cytometer to detect lymphocytes that have bound fluorescence-labeled antigen has been developed and put to practice (Altman, J. D., Moss, P. A., Goulder, P. J., Barouch, D. H., McHeyzer-Williams, M. G., Bell, J. I., McMichael, A. J., Davis, M. M., Phenotypic analysis of antigen-specific T lymphocytes, *Science*, 274: 94-96, 1996 (Nonpatent Reference 3)). This method is capable of identifying a single lymphocyte bound to antigen. It is also capable of separating out individual lymphocytes that bind antigen.

However, the above-cited method requires an expensive and complex device known as a cell sorter for separating out individual lymphocytes, and presents the following problems as well:

(1) It is difficult to set the separating conditions of the device, requiring skills for operating device to separate out cells;
(2) The background is high, precluding the detection of antigen-specific lymphocytes at frequencies of less than or equal to 0.1 percent;
(3) cell separation is inefficient;
(4) time is required to separate out cells of low frequency; and
(5) although antigen binding can be determined, it is difficult to analyze the reaction of the lymphocyte that has bound the antigen.

Another antigen-specific lymphocyte detection method has been developed in which antigen molecules bound to magnetic beads are mixed with lymphocytes to cause the magnetic bead-bound antigen to bind to the antigen receptors of the antigen-specific lymphocytes, and a magnet is then employed to separate the antigen-specific lymphocytes (Abts H., Emmerich M., Miltenyi S., Radbruch A., Tesch H. CD20 positive human B lymphocytes separated with the magnetic sorter (MACS) can be induced to proliferation and antibody secretion in vitro. Journal of Immunological Methods 125: 19-28, 1989 (Nonpatent Reference 4)).

This method requires no complex device, cells are rapidly separated, and antigen binding can be determined. However, it is not possible to analyze the reaction of the lymphocyte in binding the antigen (the metabolic or physiological reaction of the cell, such as intracellular signal transduction, RNA synthesis, or protein synthesis). Further, the antigen-specific lymphocyte cannot be detected when the frequency of the antigen-specific lymphocyte is less than or equal to 0.1 percent.

Accordingly, the present invention has as its first object to provide a method of detecting antigen-specific lymphocytes that does not require a complex device, rapidly separates cells, permits the determination of antigen binding, permits the detection of antigen-specific lymphocytes (even at 0.001 percent and above), permits analysis of whether the lymphocyte that has bound the antigen reacts with antigen, and permits the separation of antigen-specific lymphocytes.

Further objects of the present invention are to provide a microwell array chip for detecting antigen-specific lymphocytes to be employed in the above-described detection method and a method of manufacturing antigen-specific lymphocytes using the above-described detection method.

The following are conventionally known methods of cloning antigen-specific antibody genes:

(1) In humans, there exists the method in which peripheral B lymphocytes are transformed with EB virus, antigen-specific antibody-producing cells are screened from the colonized cells, and antibody genes are cloned from the antigen-specific lymphocytes (Roome, A. J., Reading, C. L. The use of Epstein-Barr virus transformation for the production of human monoclonal antibodies. Exp. Biol. 43:35-55, 1984 (Nonpatent Reference 5), Carson, D. A., Freimark, B. D. Human lymphocyte hybridomas and monoclonal antibodies. Adv. Immunol. 38:275-311, 1986 (Nonpatent Reference 6)). This method is bothersome in that the screening of antigen-specific lymphocyte cell colonies is inefficient and a whole month is required to culture the cells. Although hybridomas can be produced for mice, no efficient human hybridoma system has yet been produced.

(2) A further method exists in which bacteriophage is employed to clone antigen-specific antibody genes (Huston, J. S., Levinson D., Mudgett-Hunter, M., Tai, M. S., Novotny, J., Margolies, M. N., Ridge, R. J., Bruccoleri, R. E., Haber, E., Crea, R., et al. Protein engineering of antibody binding sites:

recovery of specific activity in an anti-digoxin single-chain Fv analogue produced in *Escherichia Coli*. Proc. Natl. Acad. Sci., U.S.A. 85:5879-5883, 1988 (Nonpatent Reference 7)). In this case, mRNA is extracted from human lymphocytes, cDNA libraries consisting of the H and L chains of immunoglobulin, respectively, are prepared, the two are combined into single phage DNA, and the H and L chains are expressed by the phage. Antigen specificity is determined by the combination of H and L chains. However, in this system, the combinations are random and the phages producing antibody binding to the antigen are screened with antigen. As a result, when a phage producing antibody binding to antigen is produced, an antigen-specific antibody gene can be cloned. However, the random combination of H and L chains renders the screening of antigen-specific antibody genes highly inefficient. For example, assuming that the H chain cDNA and L chain cDNA of antibody for a given antigen are each present in the library at a frequency of one part in $10^4$, the combination of an H chain and L chain capable of binding the antibody will be present at a frequency of one part in $10^8$. Further, in this system, it is not known whether the combinations of H and L chains obtained are actually produced in the human body.

As set forth above, conventional methods of cloning antigen-specific antibody genes are highly inefficient. Even so, with considerable effort, it is possible to clone antigen-specific antibody genes by these methods. However, it is not possible to identify and select low-frequency antigen-specific lymphocytes using conventional methods.

Accordingly, the present invention has as its object to provide a method of conveniently selecting lymphocytes reacting with specificity to a certain antigen and efficiently cloning antigen-specific antigen receptor gene from the selected antigen-specific lymphocytes, both for antigen-specific lymphocytes of relatively high frequency and those of low frequency. Further objects of the present invention are to provide a method of manufacturing monoclonal antibody from the cloned antigen-specific immunoglobulin gene, and to provide a method of manufacturing materials for gene therapy using the cloned antigen-specific T-cell receptor gene.

DISCLOSURE OF THE INVENTION

The present invention, which solves the above-stated problems, is described below.

The first aspect of the present invention relates to a microwell array chip that has multiple microwells and is employed to contain a single lymphocyte specimen in each microwell and detect antigen-specific lymphocytes in single units; wherein the microwell array chip is of a shape and of dimensions where only one lymphocyte is contained in each microwell.

In the microwell array chip of the first form of the present invention, the following are desirable:

(1) The microwell is of cylindrical, rectangular parallelepiped, inverse conical, or inverse pyramid shape, or some combination of two or more thereof.

(2) The diameter of the maximum circle inscribable in a planar configuration of the microwells falls within a range of from one to two times the diameter of the lymphocytes that are to be contained in the microwells, and the depth of the microwells falls within a range of from one to two times the diameter of the lymphocytes to be contained in the microwells.

The second form of the present invention relates to a microwell array chip that is employed to detect antigen-specific lymphocytes and has multiple microwells each containing a single lymphocyte specimen.

In the microwell array chip of the second aspect of the present invention, the following are desirable:

(1) The microwell has a diameter of from 5 to 100 micrometers and a depth of from 5 to 100 micrometers.

(2) The lymphocyte specimen is contained in the microwell together with a culture medium.

(3) The lymphocyte specimen is derived from blood.

(4) The lymphocyte specimen is a B lymphocyte or T lymphocyte.

The third aspect of the present invention relates to a method of detecting antigen-specific lymphocytes comprising the steps of adding antigen to each microwell in the microwell array chip the above-described second aspect of the present invention, stimulating the lymphocyte specimen, and detecting lymphocyte specimens reacting with the antigen.

In the method of detecting antigen-specific lymphocytes of the third form of the present invention, the following are desirable:

(1) The detection of cells reacting with antigen is conducted by using Ca ion dependent fluorescent dye.

(2) The detection of cells reacting with antigen is conducted by employing, as a marker, an activated marker protein expressed on the surface of the activated lymphocyte specimen that has been stimulated with antigen.

(3) The detection of cells reacting with antigen is conducted by employing, as an indicator, the degree of polarization of fluorescence emitted by a fluorescent substance in the lymphocyte specimen.

(4) The detection of cells reacting with antigen is conducted by employing, as an indicator, the proliferation of the lymphocyte specimen or the production of antibody.

(5) The antigen is a protein, peptide, DNA, RNA, lipid, sugar chain, or organic macromolecular compound.

(6) The antigen is a bacterium, virus, autoantigen, tumor antigen, or allergen.

The fourth aspect of the present invention relates to a method of manufacturing antigen-specific lymphocytes comprising the step of recovering from microwells lymphocyte specimens reacting with antigen that have been detected by the method of the above-described third aspect of the present invention.

The fifth aspect of the present invention relates to a method in which a single lymphocyte reacting specifically with a certain antigen (referred to hereinafter as an antigen-specific lymphocyte) is selected and an antigen-specific antigen receptor gene is cloned from the single antigen-specific lymphocyte.

In the method of cloning antigen-specific antigen receptor gene of the fifth aspect of the present invention, the following are desirable:

(1) The selection of the antigen-specific single lymphocyte is conducted by adding antigen to each microwell in an antigen-specific lymphocyte detection-use microwell array chip having multiple microwells each containing a single lymphocyte specimen, detecting which lymphocytes have reacted with the antigen, and removing the antigen-specific lymphocytes that have been detected from the microwells.

(2) The antigen-specific lymphocyte is present in a frequency of 0.1 percent or less.

(3) The antigen-specific lymphocyte is broken down using a cytolytic agent and the antigen-specific antigen receptor gene is amplified by RT-PCR.

(4) The RT-PCR is conducted by preparing cDNA with reverse transcriptase and carrying out PCR twice with primer mixes for antigen receptor gene.

(5) The antigen-specific lymphocyte is a B lymphocyte or T lymphocyte.

(6) The antigen-specific antigen receptor gene is an immunoglobulin gene when the antigen-specific lymphocyte is a B lymphocyte and a T-cell receptor gene when the antigen-specific lymphocyte is a T lymphocyte.

(7) The antigen-specific lymphocyte is a B lymphocyte and an antigen-specific immunoglobulin gene is cloned.

(8) The antigen-specific lymphocyte is a T lymphocyte and an antigen-specific T-cell receptor gene is cloned.

(9) Gene amplification is conducted in the microwell without removing from the microwell the antigen-specific lymphocyte that has been detected.

The sixth aspect of the present invention relates to a method of manufacturing monoclonal antibody using the antigen-specific immunoglobulin gene that has been cloned by the method of cloning antigen-specific antigen receptor gene of the fifth aspect of the present invention, specifically, by the method of cloning in which the antigen-specific lymphocyte is a B lymphocyte and the antigen-specific immunoglobulin gene is cloned.

The seventh aspect of the present invention relates to a method of manufacturing material for gene therapy employing the antigen-specific T-cell receptor gene that has been cloned by the method of cloning antigen-specific antigen receptor gene of the fifth aspect of the present invention, specifically, by a method of cloning in which the antigen-specific lymphocyte is a T lymphocyte and the antigen-specific T-cell receptor gene is cloned.

BRIEF DESCRIPTION OF THE FIGURES

FIG. 4 shows the results of a test of the efficiency of introduction of cells into microwells conducted by fluorescence microscopy or microarray scanning.

FIG. 9 shows a comparison of the sequence of the antibody (L chain) gene obtained in an embodiment and the sequence of antibody genes contained in an existing database.

FIG. 10 shows a comparison of the sequence of antibody (H chain) gene obtained in an embodiment and the sequence of antibody gene contained in an existing database.

BEST MODE OF IMPLEMENTING THE INVENTION

The Microwell Array Chip

Figure 1:
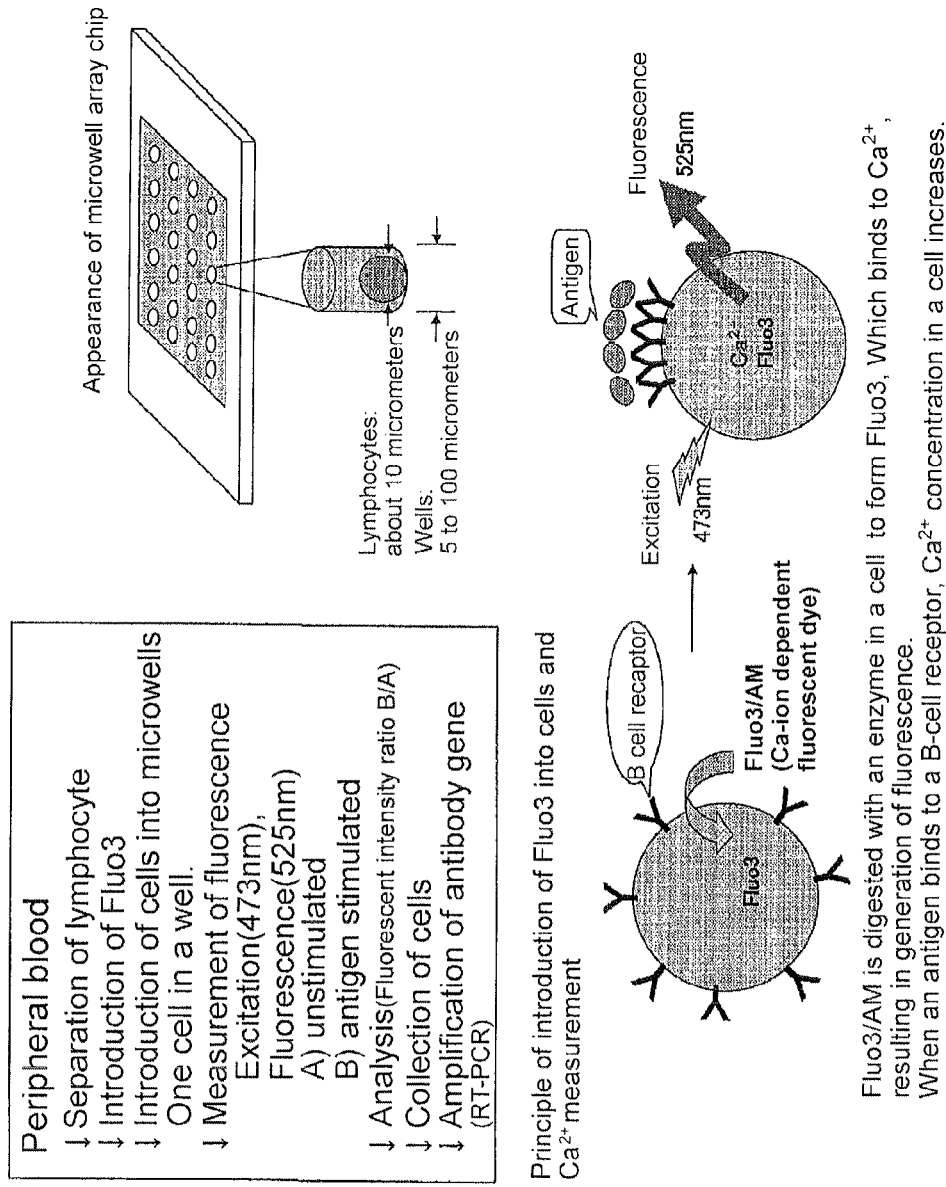
FIG. 1 is a drawing descriptive of the method of measuring change in the concentration of Ca ions within the cell using a fluorescent dye dependant on Ca ions. In particular, the introduction of Fluo3 dye into the cell and a method of detecting antigen-specific lymphocytes are described.

The microwell array chip of the present invention is a microwell array chip that has multiple microwells and is employed to contain a single lymphocyte specimen in each microwell and detect antigen-specific lymphocytes in single units. The microwell array chip is of a shape and of dimensions where only one lymphocyte is contained in each microwell.

The shape and size of the microwell are not specifically limited. However, the shape of the microwell may be, for example, cylindrical or noncylindrical. It may be that of a rectangular parallelepiped, inverse conical, or inverse pyramid shape (inverse triangular pyramid, rectangular pyramid, pentagonal pyramid, hexagonal pyramid, heptagonal pyramid, or pyramid with a greater number of angles). It may also be of a shape combining two or more of these shapes. For example, one portion may be cylindrical, while the remainder is an inverse cone. Or, in the case of an inverse cone or inverse pyramid, the bottom surface may be the opening of the microwell and its shape may be one obtained by cutting off a portion of the top of an inverse cone or inverse pyramid (in which case the bottom of the microwell is flat). For cylinders and rectangular parallelepipes, the bottom of the microwell is normally flat, but may also be in the form of a curved (convex or concave) surface. The bottom of the microwell may be in the form of a curved surface as well in the case of shapes obtained by cutting off a portion of the top of an inverse cone or inverse pyramid.

The shape and dimensions of the microwell are suitably determined in consideration of the type (shape, size, and the like) of the lymphocyte to be contained in the microwell so that a single lymphocyte can be contained in each microwell.

To permit a single lymphocyte to be contained in each microwell, for example, the diameter of the maximum circle that can be inscribed in the planar configuration of the microwell is suitably determined to fall within a range of from one to two times, preferably 1.1 to 1.9 times, and more preferably 1.2 to 1.8 times, the diameter of the lymphocyte to be contained in the microwell.

Further, the depth of the microwell is suitably determined to fall within a range of from one to two times, preferably 1.1 to 1.9 times, and more preferably 1.2 to 1.8 times the diameter of the lymphocyte to be contained in the microwell.

When the microwell is cylindrical in shape, for example, the diameter thereof can be from 5 to 100 micrometers, and when the lymphocyte is a B lymphocyte, the diameter is desirably from 5 to 15 micrometers. The depth can be from 5 to 100 micrometers, for example, and when the lymphocyte is a B lymphocyte, the depth is desirably from 5 to 40 micrometers. However, the dimensions of the microwell are suitably determined as stated above to obtain a suitable ratio of the diameter of the lymphocyte to be contained in the microwell to the size of the microwell.

The number of microwells present on each microwell array chip is not specifically limited. However, given that the frequency of antigen-specific lymphocytes is often only from 1 to at most 500 per $10^5$ lymphocytes, the number of microwells present per square centimeter can range from about 2,000 to 1,000,000, for example.

The microwell array chip for detecting antigen-specific lymphocytes of the present invention is characterized by comprising multiple microwells each of which holds a single lymphocyte specimen. The above-described microwell array chip of the present invention may be employed as is.

Since each microwell in the microwell array chip for detecting antigen-specific lymphocytes of the present invention holds just one lymphocyte specimen, it is possible to specify antigen-specific lymphocytes at the individual cell level. That is, in the method of detecting antigen-specific lymphocytes employing the microwell array chip of the present invention, since only one lymphocyte specimen is contained in each microwell, it is possible to specify the lymphocyte specimen reacting with antigen as a single cell.

As a result, it is possible to remove an antigen-specific lymphocyte that has been detected and clone the antigen-specific antibody gene or T cell receptor gene. For example, given the ability to clone antigen-specific antibody genes, it is possible to produce large amounts of human monoclonal antibody. This antibody can then be administered to an infected patient or the like to treat or prevent infection.

However, cells other than lymphocytes may also be contained along with the lymphocyte specimen in a single microwell. This is because cells other than lymphocytes do not react with antigen and are not detected.

The lymphocyte specimen is contained in the microwell with culture medium, for example. The following are examples of culture media suitable for use.

1. 137 mM NaCl, 2.7 mM KCl, 1.8 mM $CaCl_2$, 1 mM $MgCl_2$, 1 mg/mL glucose, 1 mg/mL BSA, 20 mM HEPES (pH 7.4).
2. RPMI 1640 culture medium containing 10 percent FCS (fetal calf serum).
3. RPMI 1640 culture medium 1 mg/mL BSA.
4. Dulbecco's MEM culture medium containing 10 percent FCS.
5. Dulbecco's MEM culture medium containing 1 mg/mL BSA.

The lymphocyte specimen may be derived from blood; for example, it may be a B lymphocyte or T lymphocyte. Further examples are lymphocytes derived from lymphoid tissues such as the tonsils (lymph nodes) and spleen, and lymphocytes infiltrating pathologically altered parts, such as cancer-infiltrating lymphocytes.

The Method of Detecting Antigen-Specific Lymphocytes

The method of detecting antigen-specific lymphocytes of the present invention comprises the steps of adding antigen to each of the microwells in the above described microwell array chip of the present invention, stimulating the lymphocytes, and detecting those lymphocytes reacting with the antigen.

The antigen may be added to the individual microwells in the following manner.

1. An antigen solution is supplied with a pipette in a manner covering the entire surface of the microwell array.
2. An antigen solution is supplied with an automatic spotter to each well.

The antigen that is detected by the method of detecting antigen-specific lymphocytes of the present invention is not specifically limited; examples are proteins, peptides, DNA, RNA, lipids, sugar chains, and organic macromolecular compounds (for example, environmental hormones). Further examples are bacteria, viruses, autoantigens, tumor antigens, allergens and the like.

The cells may be cultured by, for example, suspending the lymphocytes in culture medium, inserting them into microwells, and culturing them at room temperature or at 37° C. in the air or in a $CO_2$ incubator.

The cells reacting with antigen are detected by (1) using Ca ion dependent fluorescent dye, (2) using, as a marker, an activated marker protein expressed on the surface of a lymphocyte specimen that has been activated by stimulation with antigen, (3) employing, as an indicator, the degree of polarization of fluorescence generated by a fluorescent substance present within the lymphocyte specimen, and (4) employing, as an indicator, the proliferation of lymphocyte specimen cells or the generation of antibody by them.

More specifically, for example, when antigen binds to the antigen receptor (immunoglobulin) of a B lymphocyte, signal transduction first occurs within the cell, after which the cell proliferates and antibody production occurs. Accordingly, various methods may be employed to detect signal transduction within the cell, cell proliferation, and antibody production, thereby detecting cells reacting to antibody. Alternatively, for example, when antigen binds to the antigen receptor of a T lymphocyte, signal transduction first occurs within the cell, after which the cell proliferates and cytokine production occurs. Accordingly, various methods may be employed to detect signal transduction within the cell, cell proliferation, and the production of cytokine, thereby detecting cells reacting to antigen.

The detection of signal transduction within the cell to detect cells reacting with antigen, for example, can be conducted by detecting change in the concentration of Ca ions within the cell with Ca ion dependent fluorescent dyes.

When detecting change in the concentration of Ca ions within the cell, the fluorescent dye employed may be Fura-2, Fluo-3, or Fluo-4, and the detection device may be a fluorescence microscope or microarray scanner.

Specifically, as shown in FIG. 1, a Ca-ion dependent fluorescent dye such as Fura-2 or Fluo-3 is introduced into the B lymphocyte. Next, the B lymphocyte is stimulated with antigen, causing the Ca ion concentration within the B lymphocyte to rise. As a result, Ca ions bind to the Ca ion dependent fluorescent dye, and the fluorescent intensity increases. Cells with low concentration of Ca ions are shown as bluish in color and cells with high concentration of Ca ions are shown as reddish color. This method permits the use of a microwell array chip to detect B lymphocytes (antigen specificity) in which the Ca ion concentration within the cells has increased due to stimulation with antigen.

In the detection of cell proliferation, cells reacting with antigen can be detected by measuring, for example, the number of cells by using a live cell-specific fluorescent dye. In this method, specifically, B lymphocytes are stimulated with antigen and cultured in a $CO_2$ incubator at 37° C. for three days, causing the cells to proliferate. Once the cells have proliferated, fluorescein diacetate (FDA) or carboxy-fluorescein diacetate succinimidyl ester (CFSE) solution is added to the culture medium. These reagents pass through the membranes of living cells and are decomposed by esterase within the cells, producing a fluorescent dye that is incapable of passing throughout the membrane. The light emitted by this fluorescent dye is proportional to the number of cells, so the sum of the fluorescent intensity of the living cells within the well can be measured with a fluorescence microscope or microarray scanner to determine the number of living cells.

It is also possible to detect cells reacting with antigen by measuring the production of antibody. Antibody production can be detected by immunochemically measuring the antibody.

Specifically, when B lymphocytes are stimulated with antigen, incubated in a $CO_2$ incubator for 37° C., and cultured for one week, they secrete antibody into the culture medium. Antigen-specific antibody that has been secreted into the culture medium can be detected by the ELISA method (enzyme-linked immunosorbent assay).

Alternatively, it is also possible to employ mitogen, lectin, antibody, cytokine, PMA, and Ca ionophore to detect signal transduction, cell proliferation, and antibody production.

Figure 2:
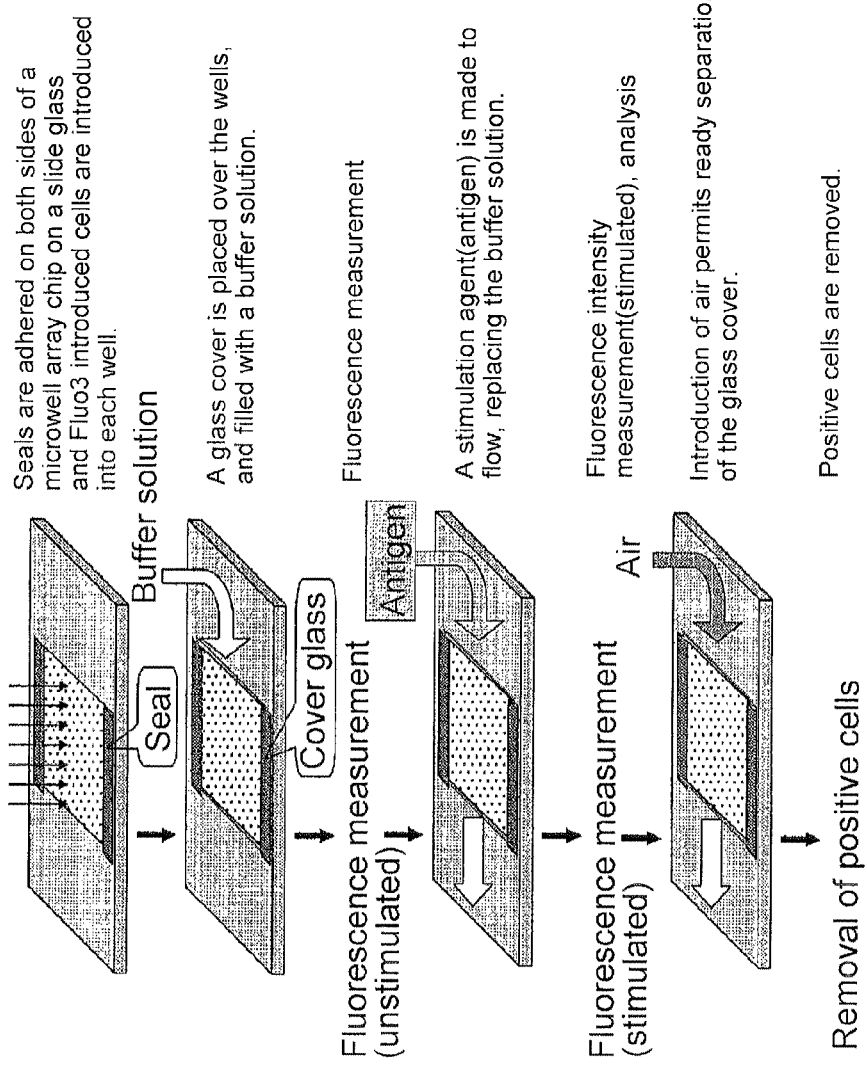
FIG. 2 is a drawing descriptive of the introduction of cells into a microwell array chip, antigen stimulation, and removal in a method employing fluorescent dye. In particular, the introduction of cells containing Fluo3 dye into the microwells is described.
Figure 3:
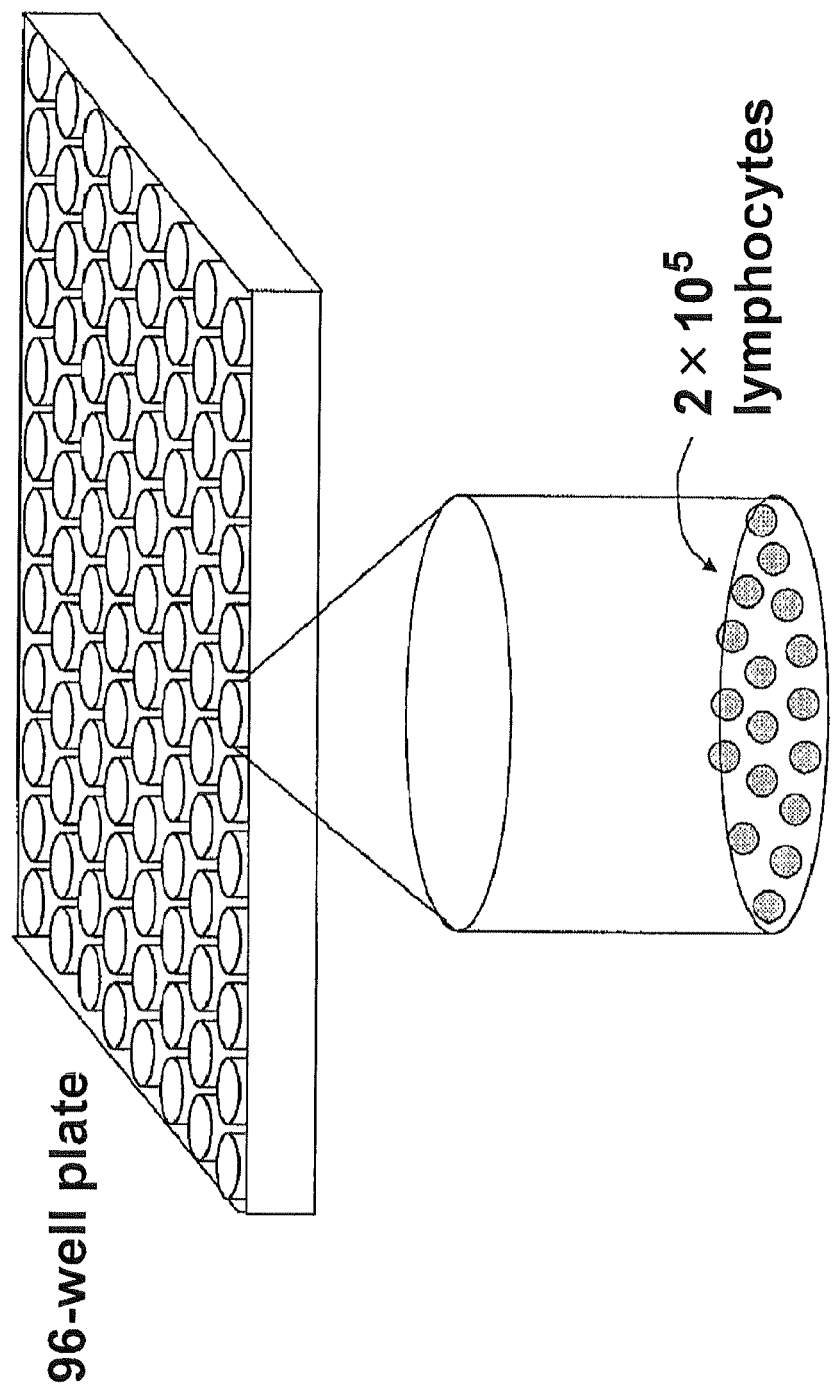
FIG. 3 is a conventional 96-well plate employed to measure antigen-specific lymphocytes.

The introduction of cells onto the microwell array chip, their stimulation with antigen, and their removal in the method employing fluorescent dye will be described below based on FIG. 2.

(1) Cell Introduction

Single cells are introduced into each microwell.

The cells introduced into the microwells are prepared, for example, by separating the lymphocyte fraction from peripheral blood, followed by further separation and purification of the B lymphocyte fraction.

Next, the cells are suspended in Fluo3/AM (2 micromole) solution, kept standing for 30 min. at room temperature, and washed with buffer solution to remove dye that has not been incorporated into the cells.

The cells loaded with Fluo3 are then introduced into the microwells. Both sides of the microwell array chip are sealed, a glass cover is placed thereover, and the space between is filled with buffer solution to prevent it from drying out.

(2) Measuring Fluorescence

First, the fluorescence of the unstimulated cells is measured and at the time, fluorescence intensity (A) is calculated. Next, an antigen solution is applied to flow between the glass slide and the glass cover, replacing the buffer solution, and the fluorescence of cells that have been stimulated by the antigen is measured. One or two minutes following stimulation, the fluorescent intensity (B) is measured. The cells in wells with a high ratio of fluorescence intensity (B/A) before and after stimulation are selected.

(3) Removal (Recovery) of Cells Reacting to Antibody Stimulation

When air is introduced between the glass slide and the glass cover, the cover glass is readily removed. Cells that have reacted due to antigen stimulation are selected based on the ratio (B/A) of fluorescence intensity of the cells after stimulation to the ratio of fluorescent intensity of the cells prior to stimulation and removed to recover antigen-specific lymphocytes.

The Method of Cloning Antigen-Specific Antigen Receptor Genes

In the cloning method of the present invention, a single lymphocyte (antigen-specific lymphocyte) specifically reacting with a certain antigen is selected, and antigen-specific antigen receptor gene is cloned from this single antigen-specific lymphocyte.

The cloning method of the present invention is particularly effective when the frequency of the antigen-specific lymphocyte is 0.1 percent or less. However, it is also suited to cases where the frequency exceeds 0.1 percent.

The antigen-specific lymphocyte may be, for example, a B lymphocyte or T lymphocyte. Further, the antigen-specific antigen receptor gene is an immunoglobulin gene when the antigen-specific lymphocyte is a B lymphocyte and a T cell receptor gene when the antigen-specific receptor gene is a T lymphocyte.

Each lymphocyte in the blood reacts with a different antigen. Accordingly, the present invention can detect a B lymphocyte specifically reacting with an antigen, and from this B lymphocyte, immunoglobulin (antibody) gene reacting with an antigen (pathogen) can be amplified by RT-PCR amplification. Similarly, a T lymphocyte specifically reacting with an antigen can be detected and from this T lymphocyte, T cell receptor gene reacting to antigen (pathogen) can be amplified by RT-PCR.

The Selection of Antigen-Specific Lymphocytes

A single antigen-specific lymphocyte can be selected by a method employing a microwell array chip, for example. In methods employing a microwell array chip, for example, antigen is added to each of the microwells of a microwell array chip having multiple microwells containing single lymphocyte specimens that is used for detecting antigen-specific lymphocytes. Next, the lymphocytes reacting with the antigen are detected, the detected antigen-specific lymphocytes are removed from the microwells, and it is possible to obtain a single antigen-specific lymphocyte. This method will be described in greater detail.

(The Microwell Array Chip)

A microwell array chip having multiple microwells each of which is capable of holding one lymphocyte specimen can be employed. Holding a single lymphocyte specimen in each microwell permits the specification of antigen-specific lymphocytes at the cell level. That is, using such a microwell array chip, since a single lymphocyte specimen is contained in each microwell, lymphocyte specimens reacting with antigen can be specified as single cells. As a result, antigen-specific lymphocytes can be detected as single cells. The single antigen-specific lymphocyte that is detected can be removed and the gene can be cloned.

However, cells other than lymphocytes may be contained in a single microwell along with the lymphocyte specimen. This is because cells other than lymphocytes do not react with antigen and are not detected.

An example of a microwell array chip is the above-described microwell array chip of the present invention.

A lymphocyte specimen is contained in the microwells together with a culture medium. Examples of culture media are given below.

1. 137 mM NaCl, 2.7 mM KCl, 1.8 mM $CaCl_2$, 1 mM $MgCl_2$, 1 mg/mL glucose, 1 mg/mL BSA, 20 mM HEPES (pH 7.4)

2. RPMI 1640 culture medium containing 10 percent FCS (fetal calf serum)

3. RPMI 1640 culture medium containing 1 mg/mL BSA

4. Dulbecco's MEM culture medium containing 10 percent FCS

5. Dulbecco's MEM culture medium containing 1 mg/mL BSA

The lymphocyte specimens may be derived from blood; for example, they may be B lymphocytes or T lymphocytes. They may also be lymphocytes derived from lymphoid tissues such as the tonsils (lymph nodes) and spleen, and lymphocytes infiltrating pathologically altered parts, such as cancer-infiltrating lymphocytes.

(The Method of Detecting Antigen-Specific Lymphocytes)

The method of detecting antigen-specific lymphocytes comprises the steps of adding antigen to each of the microwells of the above-described microwell array chip, stimulating the cells, and detecting the cells that react to the antigen.

The antigen can be added to each of the microwells in the following manner.

1. An antigen solution is added with a pipette in a manner covering the entire surface of the microwell array.

2. An antigen solution is added to each well with an automatic spotter.

The antigen that is detected by the method of detecting antigen-specific lymphocytes of the present invention is not specifically limited; examples are proteins, peptides, DNA, RNA, lipids, sugar chains, and organic macromolecular compounds. Further examples are bacteria, viruses, autoantigens, tumor antigens, allergens and the like.

The cell may be cultured, for example, by suspending the lymphocytes in culture medium, pouring the medium into microwells, and culturing at room temperature or at 37° C. in air or in a $CO_2$ incubator.

Cells reacting with antigen may be detected in the following manner.

For example, when antigen binds to the antigen receptor (immunoglobulin) of a B lymphocyte, signal transduction within the cell occurs first. This is followed by cell proliferation and antibody production. Accordingly, cells reacting with antigen can be detected by detection of internal cell signal transduction, cell proliferation, and antibody production using a number of methods. Alternatively, when antigen binds to the antigen receptor of a T lymphocyte, signal transduction within the cell occurs first. This is followed by cell proliferation and cytokine production. Accordingly, cells reacting with antigen can be identified by detection of internal cell signal transduction, cell proliferation, and cytokine production using a number of methods.

The detection of signal transduction within the cell to detect cells reacting with antigen, for example, can be conducted by detecting change in the concentration of intra-cellular Ca ions with Ca ion-dependent fluorescent dyes. When detecting change in the concentration of intra-cellular Ca ions, the fluorescent dye employed may be Fura-2 or Fluo-3, and the detection device employed may be a fluorescence microscope or microarray scanner.

Specifically, as shown in FIG. 1, a Ca ion-dependent fluorescent dye such as Fura-2 or Fluo-3 is introduced into the B lymphocyte. Next, the B lymphocyte is stimulated with an antigen, causing the Ca ion concentration within the B lymphocyte to rise. As a result, Ca ions bind to the Ca ion dependent fluorescent dye, and the fluorescent intensity increases. A cell with low concentration of Ca ions is shown with bluish color and a cell with high concentration of Ca ions is shown with reddish color. This method permits the use of a microwell array chip to detect (antigen-specific) B lymphocytes in which the Ca ion concentration within the cells has increased due to stimulation with antigen.

In the detection of cell proliferation, cells reacting with antigen can be detected by measuring, for example, the number of cells by using a live cell-specific fluorescent dye. In this method, specifically, B lymphocytes are stimulated with an antigen and cultured in a $CO_2$ incubator at 37° C. for three days, causing the cells to proliferate. Once the cells have proliferated, fluorescein diacetate (FDA) or carboxy-fluorescein diacetate succinimidyl ester (CFSE) solution is added to the culture medium. These reagents pass through the membranes of living cells and are decomposed by esterase within the cells, producing a fluorescent dye that is incapable of passing through the membrane. The light emitted by this fluorescent dye is proportional to the number of cells, so the sum of the fluorescent intensity of the living cells within the well can be measured with a fluorescence microscope or microarray scanner to determine the number of living cells.

It is also possible to detect cells reacting to antigen by measuring antibody production. Antibody production can be detected by immunochemical measurement of antibodies.

Specifically, when B lymphocytes are stimulated with antigen, cultured in a $CO_2$ incubator at 37° C. for one week, they secrete antibody into the culture medium. Antigen-specific antibody that has been secreted into the culture medium can be detected by the ELISA method (enzyme-linked immunosorbent assay).

In these detection methods, it is also possible to employ mitogen, lectin, antibody, cytokine, PMA, and Ca ionophore to detect signal transduction, cell proliferation, and antibody production.

The introduction of cells into a microwell array chip in the method employing a fluorescent dye, stimulation with antigen, and the removal of the cells will be described below based on FIG. 2.

(1) Cell Introduction

Single cells are introduced into each well.

The cells introduced into the wells are obtained, for example, by separating the lymphocyte fraction from peripheral blood, followed by further separation and purification of the B lymphocyte fraction.

Next, the cells are suspended in Fluo3/AM (2 microM) solution, kept standing for 30 min. at room temperature, and washed with buffer solution to remove the dye that has not been incorporated into the cells.

The cells loaded with fluorescent dye are then introduced into the microwells.

Both sides of the microwell array chip are sealed, a cover glass is placed thereover, and the space between microwell array chip are sealed, a cover glass is filled with buffer solution to prevent it from drying out.

(2) Measuring Fluorescence

First, the fluorescence of the unstimulated cells is measured and at the time, fluorescence intensity (A) is calculated. Next, an antigen solution is added to flow between the slide glass and the cover glass, replacing the buffer solution, and the fluorescence of cells that have been stimulated by the antigen is measured. One or two minutes following stimulation, the fluorescent intensity (B) is measured. The cells in wells with a high ratio of fluorescent intensity (B/A) before and after stimulation are selected.

(3) Removal (Recovery) of Cells Reacting to Antigen Stimulation

When air is introduced between the glass slide and the glass cover, the cover glass is readily removed. Cells that have reacted due to antigen stimulation are selected based on the ratio of fluorescent intensity (B/A) of the cells after stimulation to the ratio of fluorescent intensity of the cells prior to stimulation and removed. However, antigen-specific lymphocytes that have been selected (detected) need not be necessary removed from the microwells, remaining there for gene amplification.

(Gene Amplification)

The antigen-specific lymphocytes that have been removed are lysed with a cytolytic agent. RT-PCR is then employed to clone antigen-specific immunoglobulin (antibody) gene when the antigen-specific lymphocyte is a B lymphocyte, and to clone antigen-specific T cell receptor gene when the antigen-specific lymphocyte is a T lymphocyte.

Known cytolytic agents may be employed; examples are given below.

$1 \times 1^{st}$ strand buffer [GIBCO-BRL, attached to SuperScriptII], 0.2 mM of dNTP, 0.25 percent NP-40, 0.1 mg/mL BSA, 10 mM DTT, Random Primer 0.05 microM, 1 U/microliter RNasin.

The antigen receptor gene in B lymphocytes is identical to antibody gene and, as a protein, called as immunoglobulin. The antigen receptor is present on the surface membrane of B lymphocytes (membrane-bound immunoglobulin), and the antibody is produced as a common secretory protein (secretory immunoglobulin). The difference lies on the C terminal side of the protein. Membrane immunoglobulin has a membrane domain buried in the cell membrane and a portion extending to the cytoplasmic side. Secretory immunoglobulin is also produced by the same gene. However, as a result of alternative splicing, the C terminal side of the protein differs from membrane immunoglobulin by not having a membrane domain. Consequently, it is produced as a secretory protein.

However, the antigen binding site of these two proteins is identical. Accordingly, for B lymphocytes, antibody gene cloning and antigen receptor gene cloning are identical.

In the case of T lymphocytes, there is no secretory antigen receptor. Accordingly, there is only one clone of each antigen receptor gene. In the case of T lymphocytes, just as in the case of the primer designed for B lymphocytes, one designs primers. This is because the genomic structure of the T lymphocyte antigen receptor (TCR) is nearly identical to the genomic structure of the immunoglobulin gene of B lymphocytes. Thus, along the same line of thinking, it is possible to design primers. Accordingly, if one is able to clone the antibody gene, one can clone the TCR gene by nearly the same method.

A further example of the amplification of antigen-specific immunoglobulin gene will be described below.

An antigen-specific lymphocyte that has been removed is lysed with a cytolytic agent to obtain a solution, and this solution is used to prepare cDNA with reverse transcriptase. Next, immunoglobulin gene primer mixes are employed to conduct two cycles of PCR, permitting amplification (cloning) of the desired antigen-specific immunoglobulin gene.

Reverse transcribed cDNA can be prepared by the usual methods (for example, Sambrook J., Russell, D. W., in Molecular Cloning: A Laboratory Manual, $3^{rd}$ Ed. (Cold Spring Harbor Laboratory Press, New York, 2001).

In the present invention, the RT reaction may not be conducted with RNA that has been extracted and purified from cells, but is suited to be conducted directly with a single cell in the cytolytic solution.

(Antibody Gene Amplification by PCR)

In antibody gene amplification by PCR, the PCR reaction is implemented twice to amplify the V region gene of the antibody gene.

An antibody molecule is comprised of an H chain and an L chain. The H chain of the human antibody gene, in the germline cell system, is comprised of about 200 types of V region gene fragments, about 20 types of D fragments, and about 6 types of J fragments. When differentiated into a B lymphocyte, genetic rearrangement causes each of the V fragments, D fragments, and J fragments to recombine (V/D/J recombination) into a single antigen binding site. The same holds true for the L chain.

Each B lymphocyte expresses antibody molecules of a single antigen-specificity on the cell surface. Amplification of antigen-specific antibody gene from an antigen-specific B lymphocyte requires the use of a primer matching the various V fragment sequences.

Figure 8:
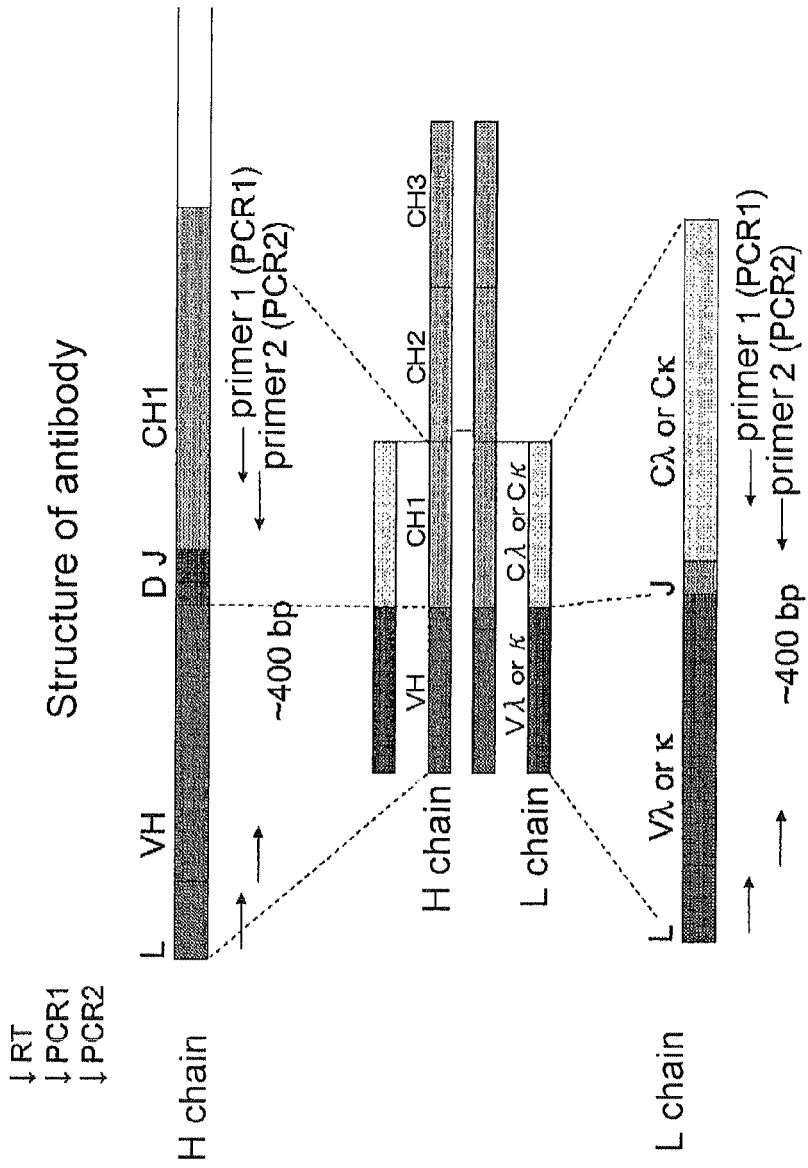
FIG. 8 is a drawing descriptive of PCR amplification of antibody gene from antigen-specific B lymphocytes.

Antibody molecules are comprised of a peptide chain of two H chains and two L chains binding to the antigen with the V regions (in the H chain, the $V_H$ chain, and in the L chain, the $V_K$ or $V_{lambda}$ region) on the left side of the schematic drawing shown in FIG. 8. The following table shows the number of subfamilies of H chains and L chains.

TABLE 1

|  |  | V region | C region |
|---|---|---|---|
| H chain |  | 7 types | 9 types* |
| L chain | Kappa chain | 7 types | 1 type |
|  | Lambda chain | 11 types | 7 types** |

As indicated in Table 1 above, the V region of the H chain of human antibody gene is divided into seven subfamilies. The sequences of the V fragments in each subfamily are quite similar, making it possible to establish a common primer. (*In the $C_H$ region, there are $C_{gamma}$ 1-4, $C_{mu}$, $C_{delta}$, $C_{alpha}$ 1-2, and $C_{epsilon}$. However, a single primer is designed for the main types of antibodies found in blood—IgG and IgM—and used in PCR. Since $C_{gamma}$ 1-4 all share a common sequence, including $C_{mu}$, two types of primer are employed. **In the $C_{lambda}$ chain, although $C_{lambda}$ chains 1 through 7 exist, only one primer of common sequence is employed.)

Since the same way of thinking can be applied for the individual subfamilies of V and C regions of the L chain, a primer is established for each subfamily, and in PCR, a mixture of all the primers of all the subfamilies of the H and L chains is employed. That is, a family in the form of a mixture of all types of H and L chains is employed.

Two cycles of PCR are conducted as set forth below to amplify the antibody gene.

The number of amino acids in the V regions of the H and L chains is about 110 to 120. Thus, the gene of the V region comprises about 400 bp.

Accordingly, as shown in FIG. 8, in PCR1, which is the first PCR cycle, cDNA is amplified from the leader sequence (L) to the C region.

In PCR2, which is the second PCR cycle, cDNA of about 400 bp inside PCR1 (from the start of the V region to the start of the C region) is amplified.

The sequence of the cDNA amplified in the second PCR cycle is analyzed.

This will be described in greater detail below.

In the present invention, the reason for using primer mixes of different sequences in PCR1 and PCR2 is as follows. Although the amplification product of PCR1 is re-amplified in PCR2, the product of PCR1 may contain both specific and nonspecific amplification products. If PCR2 is amplified with the same primer, both specific and nonspecific DNA sequences may be amplified. Accordingly, a primer of which sequence is slightly inside of the position of the primer of PCR1 in the DNA sequence amplified in PCR1 is employed in PCR2. In this manner, the nonspecific DNA sequences amplified in PCR1 are not amplified, yielding a specific DNA sequence. In addition to changing the primer and conducting a second cycle, PCR2, to amplify a specific DNA sequence, the quantity produced by a single PCR cycle is also inadequate when amplifying antibody gene from a single B lymphocyte, so two PCR cycles are employed.

In the above-described method, the cDNA sequence amplified by two PCR cycles is analyzed. In the course of the analysis, it is unnecessary to separate the first PCR cycle product from the second PCR cycle product. This is because the PCR1 product is normally negligible relative to the product amplified in PCR2.

When the antigen-specific lymphocyte is a T lymphocyte, antigen-specific T cell receptor gene is cloned. The same cloning method can be employed as for the above-described B lymphocytes. The subfamilies of antigen receptors (TCRs) of T lymphocytes are given in the following table.

TABLE 2

|  | V region | C region |
|---|---|---|
| Alpha chain | 41 types | 1 type |
| Beta chain | 30 types | 2 type |

In the cloning method of the present invention, when the antigen-specific lymphocyte is a B lymphocyte, antigen-specific immunoglobulin (antibody) gene is cloned. Then, employing the gene that has been cloned, a monoclonal antibody can be manufactured. The monoclonal antibody can be manufactured by the usual methods from the cloned gene.

PCR-amplified cDNA of the V region and the gene sequence of the C region are joined and inserted into an expression vector that is employed to obtain the antibody molecule.

As an example, it is possible to employ the monoclonal antibody manufacturing method described in Kanda, H., Mori K., Koga, H., Taniguchi, K., Kobayashi, H., Sakahara, H., Konishi, J., Endo, K., Watanabe, T. Construction and expression of chimeric antibodies by a simple replacement of heavy and light chain V genes into a single cassette vector. Hybridoma 13:359-366, 1994.

In the method of the present invention, it is unnecessary to manufacture the entire antibody molecule; it suffices to obtain the V region. Further, the sequence of genes obtained by PCR is the V region and a portion of the C region. Accordingly, the gene that is introduced into the expression vector in the method of manufacturing monoclonal antibody need not be the (entire) antibody molecule, but may be just the V region or the V region plus a portion of the C region.

The H chain and L chain are usually separately cloned. In that case, the reaction is conducted in a single tube through RT, therafter two tubes are employed for the H chain and the L chain in PCR. It is sometimes possible to synthesize both the H chain and the L chain in a single tube. However, since it is often the case where amplification of one of the chains with the ease of amplification prevails over that of the other, it is preferred to amplify the H chain and L chain in two separate tubes for reliable amplification of both chains.

Expression of both the H chain and L chain is necessary to obtain the antibody molecule. Both the H chain and the L chain are incorporated into the above-described expression vector.

In this case, in the course of separately inserting both the H chain and L chain into the expression vector and expressing the protein, two methods exist. One is simultaneous incorporation of the two expression vectors for H chain and L chain into the cell to express both the H chain and L chain in a single cell. The other is to construct an expression vector into which both the H chain and L chain have been incorporated, and then introduce the expression vector into the cell to express both the H chain and L chain in a single cell.

When introducing an expression vector into an animal cell, the antibody that is produced is precisely identical to the antibody that is produced in the human or mammalian body. When employing *E. coli*, although the amino acid sequence is precisely identical to that of the above-described antibody, there is no sugar chain attached. Since the method of the present invention produces antibody precisely identical to that produced in the human or mammalian body, production of antibody with animal cells is preferred.

In the cloning method of the present invention, when the antigen-specific lymphocyte is a T lymphocyte, antigen-specific T cell receptor gene is cloned. Using the cloned antigen-specific receptor molecule, it is possible to conduct genetic therapy. For example, it is possible to incorporate cloned T cell receptor gene into T lymphocyte or T lymphocyte precursor cells, thereby permitting the artificial production of T lymphocytes expressing specific T cell receptors in pathogens. The administration of T lymphocytes prepared in this manner to patients with diminished immune function permits the restoration of the immune function.

EMBODIMENTS

The present invention is described in greater detail below through embodiments.

Embodiment 1

1. Separation of B Lymphocytes

Employing Ficoll-Paque (Pharmacia, Uppsala, Sweden), the lymphocyte fraction was separated from peripheral blood. The B lymphocyte fraction was then further separated and purified from the lymphocyte fraction using an AutoMACS (Miltenyi Biotec, Bergisch Gladbach, Germany)

2. Introduction of Fluo3 into Cells (See FIG. 1)

$2 \times 10^6$ cells of B lymphocyte were suspended in RPMI 1640/10 percent FCS solution containing 2 micromoles of Fluo3/AM (Dojin, Kumamoto) and incubated for 30 min at room temperature. The cells were washed with RPMI 1640/10 percent FCS to remove the Fluo3/AM that had not been incorporated into the cells. Subsequently, the cells were suspended in RPMI 1640/10 percent FCS solution.

3. Microwell Array Chip (See FIG. 2)

The microwell array chip was made of poly(dimethylsiloxane) (PDMS) and had microwells of 10 micrometers in diameter and 32 micrometers in depth arranged horizontally and vertically at a spacing of 30 micrometers (the center-to-center distance of the microwells was 40 micrometers) on a 2 cm×2 cm chip. Seals with a thickness of 1 mm, a width of about 1 mm, and a length of 2 cm were attached to both sides of the microwell array chip.

4. The Microarray Scanner

The device employed was basically a Hitachi Software Engineering (K.K.) (Yokohama-shi) Microarray Scanner (CRBIO IIe-FITC) with the following changes:
(1) One of the built-in lasers (Cy3-use, 532 nm; Cy5-use, 635 nm) was replaced with a 473 nm laser.
(2) The original focal depth of ±25 micrometers was changed in this device to ±50 micrometers.

5. Detection of Activated B Lymphocyte by Microwell Array Chip (See FIG. 2)

The above-described cell suspension was added to the above-described microwell array chip and kept standing for five minutes. Cells that had not entered into microwells were washed away with RPMI 1640/10 percent FCS. The diameter of the lymphocytes was about 8 micrometers (8±1 micrometer). Since the diameter of the microwells employed was 10 micrometers, a single lymphocyte entered into each microwell. A glass cover was placed over the above-described seal and the space between the chip and the glass cover was filled with RPMI 1640/10 percent FCS solution. The microwell array chip was inserted into a microarray scanner and scanned at a resolution of 10 micrometers. The data were stored (data A: fluorescence prior to antigen stimulation).

Next, the RPMI 1640/10 percent FCS solution between the chip and the glass cover was removed and the space was filled with antigen (10 microgram/mL) dissolved in RPMI 1640/10 percent FCS solution. One minute after the antigen was added, the microwell array chip was inserted into the microarray scanner and scanned at a resolution of 10 micrometers. The data were stored (data B: fluorescence following antigen stimulation).

The ratio (B/A) of fluorescent intensity before and after stimulation was calculated and wells with high ratios were specified. Antigen-specific B lymphocytes were present in these wells.

Embodiment 2

The efficiency of introduction of cells into the microwells was examined by fluorescence microscopy or microarray scanning.

Mouse lymphocytes were fluorescently labeled with CellTracker Orange (Molecular Probe Corp.).

The mouse lymphocytes were obtained as follows.

Spleens were extracted from mice and transferred to plastic Petri dishes containing PBS. The spleens were sandwiched between two pieces of mesh and crushed to remove lymphocytes. The lymphocytes that were removed were suspended in RPMI 1640/10 percent FCS solution and the number of lymphocytes was counted.

The fluorescent labeling of the murine lymphocytes was conducted as follows.

$2 \times 10^6$ cells of B lymphocytes were suspended in loading buffer (20 mM HEPES, pH 7.4, 137 mM NaCl, 2.7 mM KCl, 1.8 mM $CaCl_2$, 1 mM $MgCl_2$, 1 mg/mL glucose, 1 mg/mL BSA) containing 1 micromole of CellTracker Orange (Molecular Probes, USA), 0.02 percent of Pluronic F-127 (Molecular Probes, USA) and incubated for 30 min with vibration at room temperature. The cells were washed with RPMI 1640/10 percent FCS solution to remove the CellTracker Orange that had not entered into the cells. The cells were then suspended in RPMI 1640/10 percent FCS.

The cell suspension (100 microliters) of fluorescently labeled mouse lymphocytes ($10^5$/microliter) was placed on a microwell array in a manner covering the array to seed the cells.

The shape and dimensions of the microarray employed were as follows.

Microwells of 10 micrometers in diameter and 12 micrometers in depth were arranged at both vertical and horizontal spacings of 15 micrometers (with center-to-center distance of 25 micrometers between microwells) on a chip of 2×2.5 cm. Seals of 1 mm thick, about 1 mm in width, and 2 cm in length were adhered to both sides of the microwell array chip.

After letting the cells sink into the wells, the cells that had not entered into wells were washed away with pipetting. It was possible to insert cells into most of the wells by repeating the series of seeding and washing operations a number of times. Finally, washing was conducted with buffer (RPMI 1640/10 percent FCS solution) so that no cells remained outside the wells. The glass cover was put in place both to prevent drying out and to render the liquid surface uniform, thereby increasing reading precision. This assembly was then observed with a fluorescence microscope (BX-URA2/BX51 W, Olympus Kogaku Kogyo, Japan) and inserted into a microarray scanner (CRBIOIIe-FITC, Hitachi Software Engineering, Japan) to read the fluorescence. The results are given in Table 4.

The diameter of the lymphocytes was 8 micrometers and the diameter of the microwells employed was 10 micrometers, so only one lymphocyte entered into each microwell. FIG. 4 shows a cluster (30×30 wells) in a portion of the chip.

The left figure shows the results of observation by fluorescence microscopy; it was confirmed that cells entered about 85 percent of the wells. The right figure shows the results of examination by microarray scanner of a different sample. Cells were confirmed to have entered about 99 percent of the wells.

Embodiment 3

Detection of Antigen-Specific B Lymphocytes by Microarray Scanner

A healthy volunteer was inoculated with hepatitis B virus vaccine and B lymphocytes were prepared from peripheral blood on days 4 and 6 by the usual methods. Human B lymphocytes were suspended in buffer (loading buffer (20 mM HEPES, pH 7.4, 137 mM NaCl, 2.7 mM KCl, 1.8 mM $CaCl_2 2H_2O$, 1 mM $MgCl_2$, 1 mg/mL glucose, 1 mg/mL BSA)) containing 4 micromoles of the calcium fluorescence indicator Fluo-4/AM (Molecular Probes Corp.), 1 micromole of CellTracker Orange (Molecular Probes Corp.), and 0.02 percent of Pluronic F-127 (Molecular Probes Corp.) to introduce Fluo-4 and CellTracker Orange into the cytoplasm. B lymphocytes loaded with Fluo-4 and CellTracker Orange were applied by the same method as in Embodiment 2 onto a microwell array chip identical to that in Embodiment 2.

Subsequently, the B lymphocytes loaded with Fluo-4 and CellTracker Orange that had been seeded in the microwell array chip were stimulated with hepatitis B virus antigen HBs protein. Following stimulation, the fluorescence of the B lymphocytes was measured with a microwell array scanner. The results are shown in FIG. 5.

The stimulation with hepatitis B virus antigen HBs protein was conducted as follows.

The RPMI 1640/10 percent FCS solution was extracted from the microwell array chip after the chip had been removed from the microwell array scanner and replaced with hepatitis B virus antigen HBs protein solution that had been diluted to 100 micrograms/mL in RPMI 1640/10 percent FCS solution. The chip was then reinserted into the microarray scanner and scanned at a resolution of 2.5 micrometers about one minute later.

Figure 5:
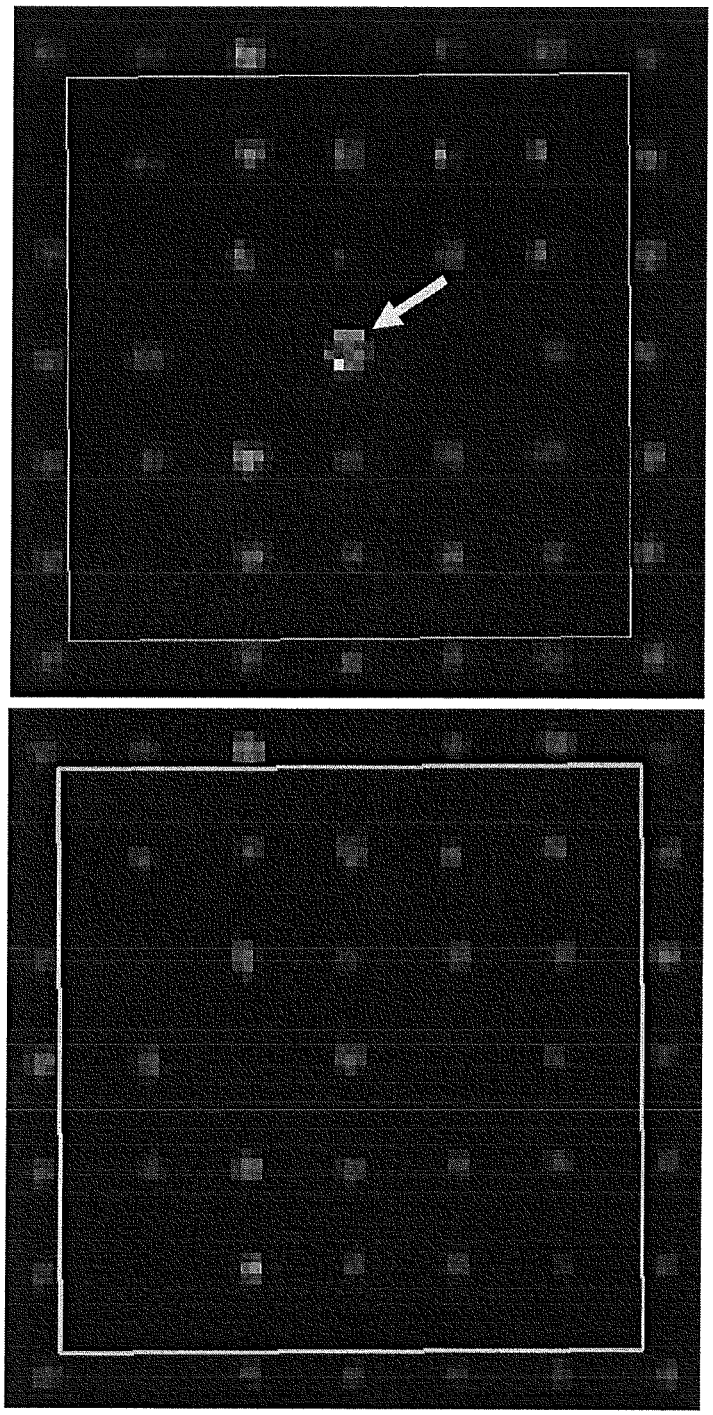
FIG. 5 shows the test results of antigen-specific B-lymphocytes by microarray scanning.

The left figure in FIG. 5 shows the fluorescent image prior to stimulation of the lymphocytes. The lymphocytes into which Fluo-4 had been introduced emitted only slight fluorescence, so the image exhibited a pale blue color. The intensity of fluorescence was also quite low.

By contrast, the right figure shows the fluorescent image after stimulation of the lymphocytes with antigen (100 micrograms/mL of hepatitis B virus antigen HBs protein). Most of the lymphocytes have undergone no change in fluorescent intensity. However, the fluorescence of antigen-specific B lymphocytes (the portion indicated by the arrow) has increased, appearing red in the image.

Observation of the fluorescence of CellTracker Orange confirmed that one cell was present in each well both before and after stimulation, and that there was no migration of cells between wells before and after stimulation (data not shown).

Figure 6:
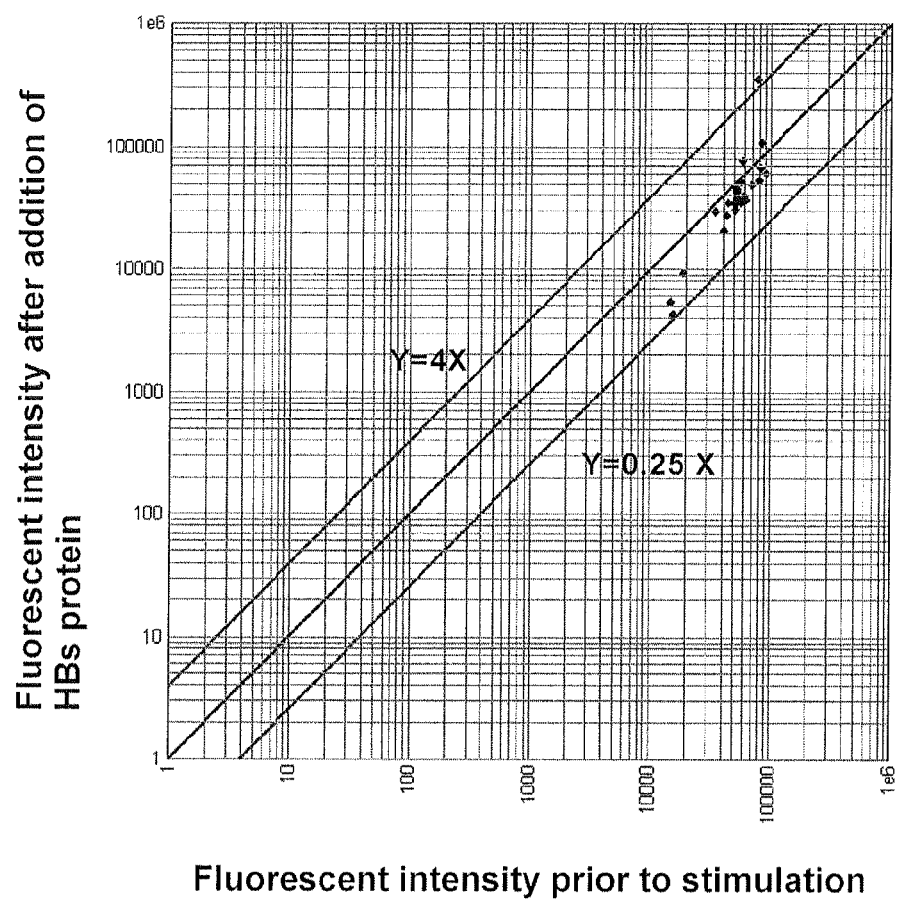
FIG. 6 is a plot of fluorescent intensity for 25 (5×5) cells enclosed in the frame shown in FIG. 5.

The measured values of the intensity of fluorescence of each of the 25 (5×5) cells enclosed by the box in FIG. 5 are plotted in FIG. 6.

The fluorescent intensity of the antigen-specific B lymphocytes (indicated by the arrow) was about 77,000 (77,454) prior to stimulation, and was about 350,000 (349,242) after stimulation, representing a roughly 4.5-fold increase. By contrast, the 24 lymphocytes that did not react to the stimulation had an average value before stimulation of 52,000 (52,683.875) and an average value after stimulation of 39,000 (38,720.833), or an average change of 0.75-fold; no significant change in intensity of fluorescence was observed.

In FIG. 6, the center straight (inclined) line shows the intensity of fluorescence when there was no change in intensity of fluorescence before and after stimulation. The two straight (inclined) lines on either side show the intensity of fluorescence when the intensity of fluorescence increased four-fold (straight line above) and one-quarter-fold (straight line below) following stimulation relative to the intensity of fluorescence prior to stimulation. The intensity of fluorescence of antigen-specific B lymphocytes (indicated by the arrow) is positioned somewhat above the straight line above. The present method, where each microwell contains a single lymphocyte, was found to be capable of detecting a single antigen-specific B lymphocyte stimulated by hepatitis B virus antigen HBs protein.

Embodiment 4

Detection of Antigen-Specific B Lymphocytes with a Microwell Array Chip

Healthy volunteers (#1, #2) in which the antibody titer for the HBs antigen of hepatitis B virus was high due to previous inoculation with hepatitis B virus vaccine were inoculated by the usual method with hepatitis B virus vaccine (10 micrograms of HBs antigen), peripheral blood was collected both before and after inoculation (days 4, 6, 8 and 10), the lymphocytes were separated, and the B lymphocytes were further separated and prepared. The B lymphocytes were labeled in the same manner as in Embodiment 3 with 4 micromoles of Fluo-4 (Molecular Probes Corp.) and 1 micromole of CellTracker Orange (Molecular Probes Corp.), applied onto a microwell array chip, and stimulated with hepatitis B virus antigen (100 micrograms/mL of HBs protein). A microarray scanner was employed to measure the fluorescence of the cells before and after stimulation with antigen. Prior to stimulation, the Fluo-4 fluorescent signal was weak. Following stimulation, the number of cells (antigen-specific B lymphocytes) for which the Fluo-4 fluorescent signal had increased was counted. Next, the fluorescence of CellTracker Orange was observed and the total number of B lymphocytes was counted. The number of cells exhibiting increased Fluo-4 fluorescence due to reaction with antigen was divided by the total number of B lymphocytes to calculate the frequency (percentage) and the results were graphed. The results are shown in FIG. 7.

The number of cells (antigen-specific B lymphocytes) exhibiting an increased fluorescence signal following stimulation was counted in the following manner.

A microarray scanner was employed to obtain fluorescent images of Fluo-4 and CellTracker Orange before and after stimulation with antigen. These were compared. In cells showing no displacement of position before and after antigen stimulation based on the fluorescent signal of the CellTracker Orange, cells that exhibited a light blue fluorescent signal of Fluo-4 prior to stimulation and in which the Fluo-4 fluorescent signal increased following stimulation, becoming red, were counted as cells in which the signal had increased (antigen-specific B lymphocytes). To calculate the frequency, the number of cells in which the fluorescent signal of Fluo-4 increased (antigen-specific B lymphocytes) was counted in five randomly selected clusters (4,500 wells). The total number of cells contained in the same five clusters (4,500 wells) was then counted based on the fluorescent image of CellTracker Orange (Molecular Probe Corp.).

Figure 7:
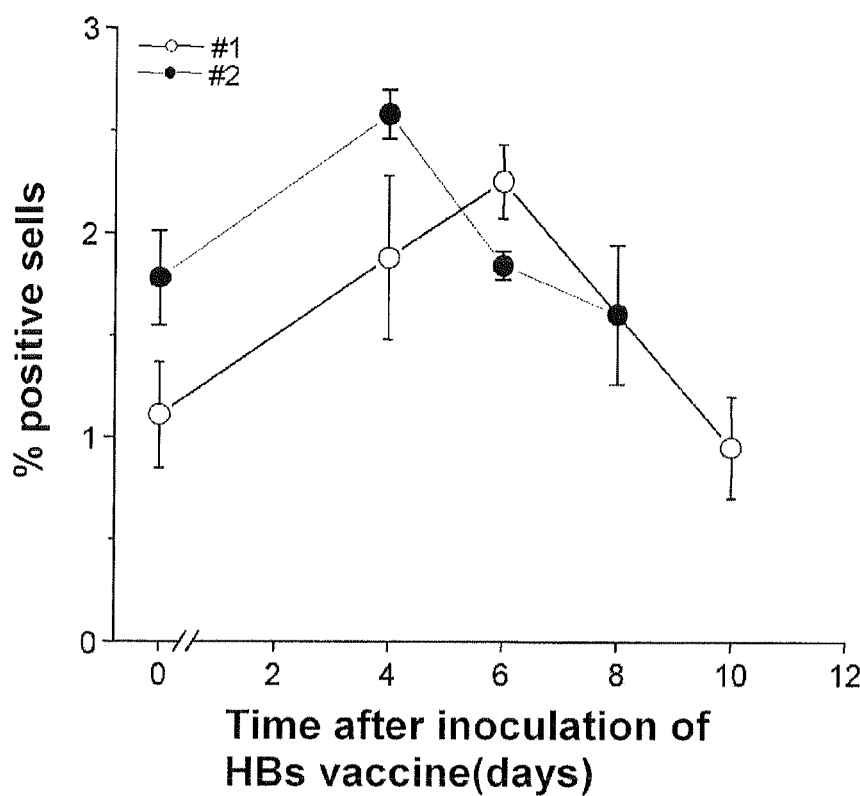
FIG. 7 shows the frequency of cells (antigen-specific B lymphocytes) in which the fluorescent signal has intensified following antigen stimulation.

The following were determined based on the results shown in FIG. 7.

1. Hepatitis B virus antigen-specific B lymphocytes in the peripheral blood of healthy volunteers whose antibody titer for HBs antigen of the hepatitis B virus was increased by inoculation with hepatitis B virus vaccine accounted for only 1 to 2 percent of the total B lymphocytes.
2. Further, at the peak 4 to 6 days after vaccine inoculation, the ratio of antigen-specific B lymphocytes to the total number of B lymphocytes increased, thereafter it dropped to the ratio that had existed prior to vaccine inoculation.
3. The present method is capable of detecting the presence or absence, frequency, and changes in antigen-specific B lymphocytes in human peripheral blood.

Embodiment 5

1. Separation of B Lymphocytes

Employing Ficoll-Paque (Pharmacia, Uppsala, Sweden), the lymphocyte fraction was separated from peripheral blood. The B lymphocyte fraction was then further separated and purified from the lymphocyte fraction using an AutoMACS (Miltenyi Biotec, Bergisch Gladbach, Germany).

2. Introduction of Fluo3 into Cells (See FIG. 1)

$2 \times 10^6$ cells of B lymphocytes were suspended in 2 micromoles of Fluo3/AM (Dojin, Kumamoto)/loading buffer (137 mM NaCl, 2.7 mM KCl, 1.8 mM $CaCl_2$, 1 mM $MgCl_2$, 1 mg/mL glucose, 1 mg/mL BSA, and 20 mM HEPES (pH 7.4)) and incubated for 30 min at room temperature. The cells were washed with loading buffer to remove the Fluo3/AM that had not been incorporated into the cells. Subsequently, the cells were suspended in RPMI 1640/10 percent FCS solution.

3. Microwell Array Chip (See FIG. 2)

The microwell array chip was made of poly(dimethylsiloxane) (PDMS) and had microwells of 10 micrometers in diameter and 32 micrometers in depth arranged horizontally and vertically at a spacing of 30 micrometers (the center-to-center distance of the microwells was 40 micrometers) on a 2×2 cm chip. Seals with a thickness of 1 mm, a width of about 1 mm, and a length of 2 cm were adhered to both sides of the chip.

4. The Microarray Scanner

The device employed was basically a Hitachi Software Engineering (K.K.) (Yokohamashi) Microarray Scanner (CRBIO IIe) with the following change: one of the built-in lasers (Cy3-use, 532 nm; Cy5-use, 635 nm) was replaced with a 473 nm laser.

5. Detection of Activated B Lymphocytes Using a Microwell Array Chip (See FIG. 2)

The above-described cell suspension was added to the above-described microwell array chip and kept standing for five minutes. Cells that had not entered microwells were washed away with RPMI 1640/10 percent FCS. The diameter of the lymphocytes was about 8 micrometers. Since the diameter of the microwells employed was 10 micrometers, a single lymphocyte entered each microwell. A glass cover was placed over the above-described seal and the space between the chip and the glass cover was filled with RPMI 1640/10 percent FCS solution. The microwell array chip was inserted into a microarray scanner and scanned at a resolution of 10 micrometers. The data were stored (data A: fluorescence prior to antigen stimulation).

Next, the RPMI 1640/10 percent FCS solution between the chip and the glass cover was removed and the space was filled with antigen (10 micrograms/mL) dissolved in RPMI 1640/10 percent FCS solution. One minute after the antigen was added, the microwell array chip was inserted into the microarray scanner and scanned at a resolution of 10 micrometers. The data were stored (data B: fluorescence following antigen stimulation).

The ratio (B/A) of fluorescent intensity before and after stimulation was calculated, and wells with high ratios were specified. Antigen-specific B lymphocytes were present in these wells.

6. Separating Out Cells from the Microwells

The cells were separated out under a microscope using a glass capillary with a micromanipulator.

7. Amplification of Antigen-Specific B Lymphocytes by PCR (See FIG. 8)

A single antigen-specific B lymphocyte was added to a PCR tube (5 microliters). To the cell was added 15.15 microliters of cytolytic solution (final concentration when added to 25 microliters: 1×1$^{st}$ strand buffer [GIBCO-BRL, attached to SuperScriptII], 0.2 mM dNTP, 0.25 percent NP-40, 0.1 mg/mL BSA, 10 mM DTT, 0.05 micromole of Random Primer, 1 U/microliter RNasin [Promega, Madison, Wis.]). To this was added the reverse transcriptase SuperScriptII (4.85 microliters, 50 U) (GIBCO-BRL, Rockville, Md.), the mixture was reacted for one hour at 37° C., and cDNA was synthesized from mRNA.

| RT-PCR reaction | |
| --- | --- |
| Cell sol. (1 cell) | 5.0 microliters |
| 1$^{st}$ strand buffer (5x) | 5.0 |
| 2.5 mM dNTP | 2.0 |
| 2.5% NP-40 | 2.5 |
| 1 mg/ml BSA | 2.5 |
| 0.1M DTT | 2.5 |
| Random primer (50 pmol/microliters) | 0.025 |
| RNase Inhibitor (RNasin 40 U/microliters) | 0.625 |
| Super Script II | 4.85(50 U) |
| Total | 25.0 microliters |

37° C. 1 h

Based on the above-described reaction, cDNA was produced with reverse transcriptase from the mRNA of a single lymphocyte.

Amplification of Antibody Gene:

The V region of the H chain of the human antibody gene is divided into seven subfamilies. Since the sequences of the V fragment in each subfamily are quite similar, it is possible to design a common primer. Primers were established for each of the subfamilies of the H chain and the L chain. Using a mixed primer comprising primers for all subfamilies of the H chain and the L chain, PCR was conducted twice as set forth below to amplify antibody gene.

In the first reaction, PCR1, 5 microliters of the above-described cDNA was added to 15 microliters of PCR mix (final concentration: 1×TAKARA ExTaq buffer, 0.25 mM dNTP, 0.5 micromole of Primer 1 per subfamily, 0.05 U/microliter of ExTaq [Takara, Kyoto]) and the mixture was reacted at 94° C. for 3 min; (94° C., 30 sec; 60° C., 1 min; 72° C., 1 min 30 sec)×40 cycles; 72° C., 5 min; and infinitely at 10° C.

| PCR1 | |
| --- | --- |
| cDNA (above-described RT reaction solution) | 5.0 microliters |
| 10x ExTaq buffer | 2.0 |
| 2.5 mM dNTP | 2.0 |
| Primer 1 5' Mix (10 micromoles each) | 1.0 |
| Primer 1 3' Mix (10 micromoles each) | 1.0 |
| H$_2$O | 7.0 |
| Takara ExTaq (0.5 U/microliter) | 2.0 |
| Total | 20.0 microliters |

94° C., 3 min.
94° C., 30 sec; 60° C., 1 min; 72° C., 1.5 min. 40 cycles
72° C., 5 min.
10° C.

The PCR1 reaction amplified the DNA sequence from the leader sequence of the immunoglobulin (antibody) gene to the constant portion (C) region.

The sequences of the primers (for the H chain) employed in the above-described reaction are given below.
Primer 1 5' Mix (10 micromoles each) (primers used for the V region)
hVH17a.1 atggactgsayytggagvdtc (SEQ ID No=1)
hVH2a.1 tccacrctcctgctrctgac (SEQ ID No=2)
hVH3a.1 gggcygagstggvttttyct (SEQ ID No=3)
hVH4a.1 tcctcctsctggtggcagct (SEQ ID No=4)
hVH5.1 tcaaccgccatcctcgccct (SEQ ID No=5)
hVH6.1 ctccttcctcatcttcctgcc (SEQ ID No=6)
Primer 1 3' Mix (10 micromoles each) (primers used for the C region)
hIGHG1-4-out agtccttgaccaggcagccca (SEQ ID No=7)
hIGHMout attctcacaggagacgagggg (SEQ ID No=8)
The sequences of the primers (for the L chain) employed in the above-described reactions are given below.

```
PCR1
5' primer
hKV12.1     atgaggstcccygctcagctc  (SEQ ID No = 9)

hKV3.1      ctcttcctcctgc-         (SEQ ID No = 10)
            tactctggc hKV45.1     ctsttsctytggatctctg    (SEQ ID No = 11)

hKV6.1      tgggtttctgctgctctggg   (SEQ ID No = 12)

hKV7.1      atagggtccggggctccttg   (SEQ ID No = 13)

hLV12.1     cykctsctcctcactctcctc  (SEQ ID No = 14)

hLV3.1      ttctcctcctcggcctcctct  (SEQ ID No = 15)

hLV4.2-2    ccagcytgtgctgactcaatc  (SEQ ID No = 16)

hLV789.2    tcycagmctgtgstgacycag  (SEQ ID No = 17)

hLV6.1      ttttatgctgactcagcccc   (SEQ ID No = 18)

hLV7.1      ggcctggactc-           (SEQ ID No = 19)
            ctctctttctg hLV8.1      ggcctggatgatgcttctc-   (SEQ ID No = 20)
            ctc hLV9.1      tcctctgctcctcacctcct   (SEQ ID No = 21)
```

```
hLV10.1      cctgggtcatgctcctcctga  (SEQ ID No = 22)

hLV11.1      gcctgggctccactacttctc  (SEQ ID No = 23)

3' primer
hIGK1        ctgctcatcagatggcggga   (SEQ ID No = 24)

hIGL1        gacacacyagtgtggccttgt  (SEQ ID No = 25)
```

In the PCR2 reaction, 2 microliters of the PCR1 reaction solution were added to 18 microliters of PCR mix (final concentration: 1×TAKARA ExTaq buffer, 0.25 mM dNTP, 0.5 micromole of Primer 2 per subfamily, ExTaq 0.05 U/microliter) and the mixture was reacted at 94° C. for 3 min; (94° C., 30 sec; 60° C., 1 min; 72° C., 1 min 30 sec)×40 cycles; 72° C., 5 min; and infinitely at 10° C.

| PCR2 | |
|---|---|
| PCR 1 sol. | 2.0 |
| 10x ExTaq buffer | 2.0 |
| 2.5 mM dNTP | 2.0 |
| Primer 2 5' Mix (10 micromoles each) | 1.0 |
| Primer 2 3' Mix (10 micromoles each) | 1.0 |
| H$_2$O | 10.0 |
| Takara ExTaq (0.5 U/microliter) | 2.0 |
| Total | 20.0 |

94° C., 3 min.
94° C., 30 sec; 60° C., 1 min; 72° C., 1.5 min. 40 cycles
72° C., 5 min.
10° C.

The PCR2 reaction amplified from its variable region (V$_H$) to its constant region of the DNA sequence of the immunoglobulin (antibody) gene that had been amplified by PCR1.

The sequences of the primers (for the H chain) employed in the above-described reaction are given below.

```
Primer 2 Mix
Primer 2 5' Mix (10 micromoles each)
hVH17a.2     ggtgcagctkgtrcartctgg  (SEQ ID No = 26)

hVH2a.2      caccttgarggagtctggtcc  (SEQ ID No = 27)

hVH3a.2      aggtdcarctgktggagtcyg  (SEQ ID No = 28)

hVH4a.2      ggtcctgtcycagstgcagct  (SEQ ID No = 29)

hVH5a.2      gtgcagctggtgcagtctgg   (SEQ ID No = 30)

hVH6.2       gcagcagtcaggtccaggact  (SEQ ID No = 31)

Primer 2 3' Mix (10 µM each)
hIGHG1-4s    aagacsgatgggcccttggtg  (SEQ ID No = 32)

hIGHM        aagggttgggcggatgcact   (SEQ ID No = 33)
```

The sequences of the primers (for the L chain) employed in the above-described reaction are given below.

```
PCR2
5' primer
hKV1.2       ccagatgacccagtctccatc  (SEQ ID No = 34)

hKV2.2       ccagtggggatattgtgat-   (SEQ ID No = 35)
             gac hKV3.2       cagtctccagccaccctgtct  (SEQ ID No = 36)

hKV4.2       gtgatgacccagtctccagac  (SEQ ID No = 37)

hKV5.2       acactcacgcagtctccagca  (SEQ ID No = 38)

hKV67.2      ttgtgctgacycagtctccag  (SEQ ID No = 39)

hLV1.2       agtctgtgctgacgcagccgc  (SEQ ID No = 40)

hLV23.2      tgactcagccwcyctcmgt-   (SEQ ID No = 41)
             gtc hLV4.2-3     caatcatcctctgcmtctgc   (SEQ ID No = 42)

hLV5.2-2     gactcagccaacctccctctc  (SEQ ID No = 43)

hLV6.2       gactcagccccactctgtgtc  (SEQ ID No = 44)

hLV789.2     tcycagmctgtgstgacycag  (SEQ ID No = 45)

hLV1011.2    tgactcagccmcmctckgt-   (SEQ ID No = 46)
             gtc

3' primer
hIGK2        gacagatggtgcagccacagt  (SEQ ID No = 47)

hIGL2        cttgragctcctcagag-     (SEQ ID No = 48)
             gaggg
```

The PCR product was analyzed with agarose gel, purified, cloned with pT7Blue-T vector (Novagen, Madison, Wis.), and the antibody gene sequence was determined. A comparison with antibody gene sequences in existing databases is shown in FIGS. 9 and 10. FIG. 9 shows L chain sequences and FIG. 10 shows H chain sequences. In both of these figures, the base sequence given above is the sequence of an actual antibody gene that was amplified by RT-PCR from a single B lymphocyte, and the base sequence given below is an existing sequence recorded in a database.

FIG. 9
1$^{st}$ Nucleotide Sequence (Sequenced Antibody Gene)
  File Name: L1 (SEQ ID No.=49)
2$^{nd}$ Nucleotide Sequence (Existing Sequence)
  File Name: L33038 (SEQ ID No.=50)

FIG. 10
1$^{st}$ Nucleotide Sequence (Sequenced Antibody Gene)
  File Name: H1 (SEQ ID No.=51)
2$^{nd}$ Nucleotide Sequence (Existing Sequence)
  File Name: AF062204 (SEQ ID No.=52)

The 94 percent in FIG. 9 and the 98 percent in FIG. 10 indicate the homology between the sequenced antibody gene and the existing sequence. Based on the homology values, it is presumed that the sequenced antibody gene and the existing sequence were antibodies corresponding to different antigens.

INDUSTRIAL APPLICABILITY

In the present invention, single lymphocytes in the blood are added to single microwells and the lymphocytes are stimulated with antigen. The antigen referred to here is a pathogen such as the bacterium or virus of an infectious disease. Each of the lymphocytes in the blood reacts with different antigens. Using the microwell array chip of the present invention, it is possible to detect a lymphocyte reacting with an antigen, for example. Further, it is possible to recover the antigen-specific B lymphocyte that is detected. Recovery of the antigen-specific lymphocyte permits the amplification by PCR or the like of the antibody gene reacting with an antigen (pathogen) in a separate tube from the microwell. It is also possible to amplify the antibody gene reacting with the antigen (pathogen) within the microwell in which the antigen-specific B lymphocyte was detected.

The method of detecting antigen-specific lymphocytes of the present invention employs a microwell array chip. Thus, since the antigen-specific lymphocyte that is detected is present in a microwell, the processing (separation and DNA/RNA preparation) of the cell is easy. Further, the response of the cell to antigen can be detected. It is possible to analyze the response of the cell not just to antigen, but also to various stimuli, and to analyze the effects of various reagents on the cell response.

By detecting pathogen-specific lymphocytes and cloning pathogen-specific antibody genes, antibody treatment methods employing antibodies can be anticipated for infectious diseases. By detecting tumor-specific lymphocytes and cloning tumor-specific antibody genes and tumor-specific T cell receptor genes, antibody treatment methods employing antibodies and gene therapies employing T cell receptor genes can be anticipated for cancer.

For autoimmune disease, by detecting autoreactive lymphocytes and cloning autoantigen-specific antibody genes or T cell receptor genes, and for allergies, by detecting allergen-specific lymphocytes and cloning IgE genes, it will be possible to accurately understand pathogenesis and condition of disease, and treat patients according to pathogenesis and monitor treatment effects.

Further, by monitoring the antibody genes and T cell receptor genes collectively possessed by individuals in all lymphocytes, tailored medical treatment applications become possible through the monitoring of the immunofunctions of Japanese and Chinese herbal medicine and anticipating immunoresponses to pathogens.

What is claimed is:

1. A method of cloning an antigen-specific antigen receptor gene, comprising the steps of:
   (a) providing a microwell array having multiple microwells which contain lymphocytes, wherein said microwells are of a shape and of dimensions where only one lymphocyte can be contained in each microwell;
   (b) supplying antigen to said microwell array;
   (c) detecting said microwells containing lymphocytes that have been stimulated and are reacting with said antigen;
   (d) recovering a single lymphocyte that is an antigen-specific lymphocyte reacting with said antigen from one of said detected microwells; and
   (e) cloning at least an antigen-specific antigen receptor gene from said selected single antigen-specific lymphocyte, wherein said antigen-specific lymphocyte is a B lymphocyte.

2. The method of claim 1, wherein a glass cover is placed on the top of the microwells into which cells have been loaded to prevent the microwells from drying out.

3. The method of claim 1, wherein step (b) comprises supplying an antigen solution in a manner that covers the surface of the microwell array.

4. The method of claim 1, wherein step (b) comprises supplying an antigen solution to each well.

5. The method of claim 1, wherein antigen-specific lymphocytes present in said microwells of said microwell array occur at a frequency of 0.1 percent or less among the lymphocytes present in said array.

6. The method of claim 1, wherein said cloning comprises the steps of breaking down said antigen-specific lymphocyte using a cytolytic agent and amplifying said antigen-specific antigen receptor gene by RT-PCR.

7. The method of claim 6, wherein said RT-PCR is conducted by preparing cDNA with reverse transcriptase and carrying out PCR twice with primer mixes for the antigen-specific antigen receptor gene.

8. The method of claim 1, wherein said antigen-specific antigen receptor gene is an immunoglobulin gene.

9. The method of claim 6, wherein said antigen-specific antigen receptor gene amplification is conducted directly in the microwell containing the detected antigen-specific lymphocyte.

10. The method of claim 2, wherein a buffer solution fills the space between the glass cover and the microwells.

11. The method of claim 2, wherein the detection of the lymphocytes that have been reacted with the antigen is conducted with the glass cover in place.

* * * * *

SEQUENCE LISTING

```
<160> NUMBER OF SEQ ID NOS: 52

<210> SEQ ID NO 1
<211> LENGTH: 21
<212> TYPE: DNA
<213> ORGANISM: Artificial Sequence
<220> FEATURE:
<223> OTHER INFORMATION: H chain primer sequence, hVH17a.1

<400> SEQUENCE: 1
atggactgsa yytggagvdt c                                             21

<210> SEQ ID NO 2
<211> LENGTH: 20
<212> TYPE: DNA
<213> ORGANISM: Artificial Sequence
<220> FEATURE:
<223> OTHER INFORMATION: H chain primer sequence, hVH2a.1

<400> SEQUENCE: 2
tccacrctcc tgctrctgac                                               20

<210> SEQ ID NO 3
<211> LENGTH: 20
<212> TYPE: DNA
<213> ORGANISM: Artificial Sequence
<220> FEATURE:
<223> OTHER INFORMATION: H chain primer sequence, hVH3a.1

<400> SEQUENCE: 3
gggcygagst ggvttttyct                                               20

<210> SEQ ID NO 4
<211> LENGTH: 20
<212> TYPE: DNA
<213> ORGANISM: Artificial Sequence
<220> FEATURE:
<223> OTHER INFORMATION: H chain primer sequence, hVH4a.1

<400> SEQUENCE: 4
tcctcctsct ggtggcagct                                               20

<210> SEQ ID NO 5
<211> LENGTH: 20
<212> TYPE: DNA
<213> ORGANISM: Artificial Sequence
<220> FEATURE:
```

<223> OTHER INFORMATION: H chain primer sequence, hVH5.1

<400> SEQUENCE: 5
tcaaccgcca tcctcgccct                                                   20

<210> SEQ ID NO 6
<211> LENGTH: 21
<212> TYPE: DNA
<213> ORGANISM: Artificial Sequence
<220> FEATURE:
<223> OTHER INFORMATION: H chain primer sequence, hVH6.1

<400> SEQUENCE: 6
ctccttcctc atcttcctgc c                                                 21

<210> SEQ ID NO 7
<211> LENGTH: 21
<212> TYPE: DNA
<213> ORGANISM: Artificial Sequence
<220> FEATURE:
<223> OTHER INFORMATION: C chain primer sequence, hIGHG1-4out

<400> SEQUENCE: 7
agtccttgac caggcagccc a                                                 21

<210> SEQ ID NO 8
<211> LENGTH: 21
<212> TYPE: DNA
<213> ORGANISM: Artificial Sequence
<220> FEATURE:
<223> OTHER INFORMATION: C chain primer sequence, hIGHMout

<400> SEQUENCE: 8
attctcacag gagacgaggg g                                                 21

<210> SEQ ID NO 9
<211> LENGTH: 21
<212> TYPE: DNA
<213> ORGANISM: Artificial Sequence
<220> FEATURE:
<223> OTHER INFORMATION: L chain primer sequence, hKV12.1

<400> SEQUENCE: 9
atgaggstcc cygctcagct c                                                 21

<210> SEQ ID NO 10
<211> LENGTH: 22
<212> TYPE: DNA
<213> ORGANISM: Artificial Sequence
<220> FEATURE:
<223> OTHER INFORMATION: L chain primer sequence, hKV3.1

<400> SEQUENCE: 10
ctcttcctcc tgctactctg gc                                                22

<210> SEQ ID NO 11
<211> LENGTH: 19
<212> TYPE: DNA
<213> ORGANISM: Artificial Sequence
<220> FEATURE:
<223> OTHER INFORMATION: L chain primer sequence, hKV45.1

<400> SEQUENCE: 11
ctsttsctyt ggatctctg                                                    19

<210> SEQ ID NO 12

```
<211> LENGTH: 20
<212> TYPE: DNA
<213> ORGANISM: Artificial Sequence
<220> FEATURE:
<223> OTHER INFORMATION: L chain primer sequence, hKV6.1

<400> SEQUENCE: 12
tgggtttctg ctgctctggg                                              20

<210> SEQ ID NO 13
<211> LENGTH: 21
<212> TYPE: DNA
<213> ORGANISM: Artificial Sequence
<220> FEATURE:
<223> OTHER INFORMATION: L chain primer sequence, hKV7.1

<400> SEQUENCE: 13
atagggtccg gggctccttt g                                            21

<210> SEQ ID NO 14
<211> LENGTH: 21
<212> TYPE: DNA
<213> ORGANISM: Artificial Sequence
<220> FEATURE:
<223> OTHER INFORMATION: L chain primer sequence, hLV12.1

<400> SEQUENCE: 14
cykctsctcc tcactctcct c                                            21

<210> SEQ ID NO 15
<211> LENGTH: 21
<212> TYPE: DNA
<213> ORGANISM: Artificial Sequence
<220> FEATURE:
<223> OTHER INFORMATION: L chain primer sequence, hLV3.1

<400> SEQUENCE: 15
ttctcctcct cggcctcctc t                                            21

<210> SEQ ID NO 16
<211> LENGTH: 21
<212> TYPE: DNA
<213> ORGANISM: Artificial Sequence
<220> FEATURE:
<223> OTHER INFORMATION: L chain primer sequence, hLV4.2-2

<400> SEQUENCE: 16
ccagcytgtg ctgactcaat c                                            21

<210> SEQ ID NO 17
<211> LENGTH: 21
<212> TYPE: DNA
<213> ORGANISM: Artificial Sequence
<220> FEATURE:
<223> OTHER INFORMATION: L chain primer sequence, hLV789.2

<400> SEQUENCE: 17
tcycagmctg tgstgacyca g                                            21

<210> SEQ ID NO 18
<211> LENGTH: 20
<212> TYPE: DNA
<213> ORGANISM: Artificial Sequence
<220> FEATURE:
<223> OTHER INFORMATION: L chain primer sequence, hLV6.1

<400> SEQUENCE: 18
```
ttttatgctg actcagcccc                                          20

<210> SEQ ID NO 19
<211> LENGTH: 22
<212> TYPE: DNA
<213> ORGANISM: Artificial Sequence
<220> FEATURE:
<223> OTHER INFORMATION: L chain primer sequence, hLV7.1

<400> SEQUENCE: 19
ggcctggact cctctctttc tg                                       22

<210> SEQ ID NO 20
<211> LENGTH: 22
<212> TYPE: DNA
<213> ORGANISM: Artificial Sequence
<220> FEATURE:
<223> OTHER INFORMATION: L chain primer sequence, hLV8.1

<400> SEQUENCE: 20
ggcctggatg atgcttctcc tc                                       22

<210> SEQ ID NO 21
<211> LENGTH: 21
<212> TYPE: DNA
<213> ORGANISM: Artificial Sequence
<220> FEATURE:
<223> OTHER INFORMATION: L chain primer sequence, hLV9.1

<400> SEQUENCE: 21
tcctctgctc ctcaccctcc t                                        21

<210> SEQ ID NO 22
<211> LENGTH: 21
<212> TYPE: DNA
<213> ORGANISM: Artificial Sequence
<220> FEATURE:
<223> OTHER INFORMATION: L chain primer sequence, hLV10.1

<400> SEQUENCE: 22
cctgggtcat gctcctcctg a                                        21

<210> SEQ ID NO 23
<211> LENGTH: 21
<212> TYPE: DNA
<213> ORGANISM: Artificial Sequence
<220> FEATURE:
<223> OTHER INFORMATION: L chain primer sequence, hLV11.1

<400> SEQUENCE: 23
gcctgggctc cactacttct c                                        21

<210> SEQ ID NO 24
<211> LENGTH: 20
<212> TYPE: DNA
<213> ORGANISM: Artificial Sequence
<220> FEATURE:
<223> OTHER INFORMATION: L chain primer sequence, hIGK1

<400> SEQUENCE: 24
ctgctcatca gatggcggga                                          20

<210> SEQ ID NO 25
<211> LENGTH: 21
<212> TYPE: DNA
<213> ORGANISM: Artificial Sequence
<220> FEATURE:

<223> OTHER INFORMATION: L chain primer sequence, hIGL1

<400> SEQUENCE: 25
gacacacyag tgtggccttg t                    21

<210> SEQ ID NO 26
<211> LENGTH: 21
<212> TYPE: DNA
<213> ORGANISM: Artificial Sequence
<220> FEATURE:
<223> OTHER INFORMATION: H chain primer sequence, hVH17a.2

<400> SEQUENCE: 26
ggtgcagctk gtrcartctg g                    21

<210> SEQ ID NO 27
<211> LENGTH: 21
<212> TYPE: DNA
<213> ORGANISM: Artificial Sequence
<220> FEATURE:
<223> OTHER INFORMATION: H chain primer sequence, hVH2a.2

<400> SEQUENCE: 27
caccttgarg gagtctggtc c                    21

<210> SEQ ID NO 28
<211> LENGTH: 21
<212> TYPE: DNA
<213> ORGANISM: Artificial Sequence
<220> FEATURE:
<223> OTHER INFORMATION: H chain primer sequence, hVH3a.2

<400> SEQUENCE: 28
aggtdcarct gktggagtcy g                    21

<210> SEQ ID NO 29
<211> LENGTH: 21
<212> TYPE: DNA
<213> ORGANISM: Artificial Sequence
<220> FEATURE:
<223> OTHER INFORMATION: H chain primer sequence, hVH4a.2

<400> SEQUENCE: 29
ggtcctgtcy cagstgcagc t                    21

<210> SEQ ID NO 30
<211> LENGTH: 20
<212> TYPE: DNA
<213> ORGANISM: Artificial Sequence
<220> FEATURE:
<223> OTHER INFORMATION: H chain primer sequence, hVH5a.2

<400> SEQUENCE: 30
gtgcagctgg tgcagtctgg                      20

<210> SEQ ID NO 31
<211> LENGTH: 21
<212> TYPE: DNA
<213> ORGANISM: Artificial Sequence
<220> FEATURE:
<223> OTHER INFORMATION: H chain primer sequence, hVH6.2

<400> SEQUENCE: 31
gcagcagtca ggtccaggac t                    21

<210> SEQ ID NO 32

```
<211> LENGTH: 21
<212> TYPE: DNA
<213> ORGANISM: Artificial Sequence
<220> FEATURE:
<223> OTHER INFORMATION: H chain primer sequence, hIGHG1-4s

<400> SEQUENCE: 32
aagacsgatg ggcccttggt g                                              21

<210> SEQ ID NO 33
<211> LENGTH: 20
<212> TYPE: DNA
<213> ORGANISM: Artificial Sequence
<220> FEATURE:
<223> OTHER INFORMATION: H chain primer sequence, hIGHM

<400> SEQUENCE: 33
aagggttggg cggatgcact                                                20

<210> SEQ ID NO 34
<211> LENGTH: 21
<212> TYPE: DNA
<213> ORGANISM: Artificial Sequence
<220> FEATURE:
<223> OTHER INFORMATION: L chain primer sequence, hKV1.2

<400> SEQUENCE: 34
ccagatgacc cagtctccat c                                              21

<210> SEQ ID NO 35
<211> LENGTH: 22
<212> TYPE: DNA
<213> ORGANISM: Artificial Sequence
<220> FEATURE:
<223> OTHER INFORMATION: L chain primer sequence, hKV2.2

<400> SEQUENCE: 35
ccagtgggga tattgtgatg ac                                             22

<210> SEQ ID NO 36
<211> LENGTH: 21
<212> TYPE: DNA
<213> ORGANISM: Artificial Sequence
<220> FEATURE:
<223> OTHER INFORMATION: L chain primer sequence, hKV3.2

<400> SEQUENCE: 36
cagtctccag ccaccctgtc t                                              21

<210> SEQ ID NO 37
<211> LENGTH: 21
<212> TYPE: DNA
<213> ORGANISM: Artificial Sequence
<220> FEATURE:
<223> OTHER INFORMATION: L chain primer sequence, hKV4.2

<400> SEQUENCE: 37
gtgatgaccc agtctccaga c                                              21

<210> SEQ ID NO 38
<211> LENGTH: 21
<212> TYPE: DNA
<213> ORGANISM: Artificial Sequence
<220> FEATURE:
<223> OTHER INFORMATION: L chain primer sequence, hKV5.2

<400> SEQUENCE: 38
```
acactcacgc agtctccagc a                                              21

<210> SEQ ID NO 39
<211> LENGTH: 21
<212> TYPE: DNA
<213> ORGANISM: Artificial Sequence
<220> FEATURE:
<223> OTHER INFORMATION: L chain primer sequence, hKV67.2

<400> SEQUENCE: 39
ttgtgctgac ycagtctcca g                                              21

<210> SEQ ID NO 40
<211> LENGTH: 21
<212> TYPE: DNA
<213> ORGANISM: Artificial Sequence
<220> FEATURE:
<223> OTHER INFORMATION: L chain primer sequence, hLV1.2

<400> SEQUENCE: 40
agtctgtgct gacgcagccg c                                              21

<210> SEQ ID NO 41
<211> LENGTH: 22
<212> TYPE: DNA
<213> ORGANISM: Artificial Sequence
<220> FEATURE:
<223> OTHER INFORMATION: L chain primer sequence, hLV23.2

<400> SEQUENCE: 41
tgactcagcc wcyctcmgtg tc                                             22

<210> SEQ ID NO 42
<211> LENGTH: 20
<212> TYPE: DNA
<213> ORGANISM: Artificial Sequence
<220> FEATURE:
<223> OTHER INFORMATION: L chain primer sequence, hLV4.2-3

<400> SEQUENCE: 42
caatcatcct ctgcmtctgc                                                20

<210> SEQ ID NO 43
<211> LENGTH: 21
<212> TYPE: DNA
<213> ORGANISM: Artificial Sequence
<220> FEATURE:
<223> OTHER INFORMATION: L chain primer sequence, hLV5.2-2

<400> SEQUENCE: 43
gactcagcca acctccctct c                                              21

<210> SEQ ID NO 44
<211> LENGTH: 21
<212> TYPE: DNA
<213> ORGANISM: Artificial Sequence
<220> FEATURE:
<223> OTHER INFORMATION: L chain primer sequence, hLV6.2

<400> SEQUENCE: 44
gactcagccc cactctgtgt c                                              21

<210> SEQ ID NO 45
<211> LENGTH: 21
<212> TYPE: DNA
<213> ORGANISM: Artificial Sequence
<220> FEATURE:

<223> OTHER INFORMATION: L chain primer sequence, hLV789.2

<400> SEQUENCE: 45
tcycagmctg tgstgacyca g                                            21

<210> SEQ ID NO 46
<211> LENGTH: 22
<212> TYPE: DNA
<213> ORGANISM: Artificial Sequence
<220> FEATURE:
<223> OTHER INFORMATION: L chain primer sequence, hLV1011.2

<400> SEQUENCE: 46
tgactcagcc mcmctckgtg tc                                           22

<210> SEQ ID NO 47
<211> LENGTH: 21
<212> TYPE: DNA
<213> ORGANISM: Artificial Sequence
<220> FEATURE:
<223> OTHER INFORMATION: L chain primer sequence, hIGK2

<400> SEQUENCE: 47
gacagatggt gcagccacag t                                            21

<210> SEQ ID NO 48
<211> LENGTH: 22
<212> TYPE: DNA
<213> ORGANISM: Artificial Sequence
<220> FEATURE:
<223> OTHER INFORMATION: L chain primer sequence, hIGL2

<400> SEQUENCE: 48
cttgragctc ctcagaggag gg                                           22

<210> SEQ ID NO 49
<211> LENGTH: 335
<212> TYPE: DNA
<213> ORGANISM: Homo sapiens
<220> FEATURE:
<221> NAME/KEY: misc_feature
<222> LOCATION: (1)..(335)
<223> OTHER INFORMATION: Human antibody
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t

```
<400> SEQUENCE: 49
cagtctccag ccaccctgtc tttgtctcca ggggcaaagt agccaccctc tcctgcngggg      60 ccagtcagag tgttagcanc tacttagcct ggtaccaaca gaaacactgg ccaggctccc     120
aggctcctna tctatgatgc atctcaacag ggccactggc atcccagcca ggttaagtgg     180
cagtgggtct gggacagact tcactctcac catcancagc ctagagcctg aagattntgc     240
agttnattac tgtcancagc gtatcaactg gcctctcact ttcggcggag ggaccaaggc     300
tggagatcaa acgaactgtg gctgcaccat ctgtc                                335

<210> SEQ ID NO 50
<211> LENGTH: 330
<212> TYPE: DNA
<213> ORGANISM: Homo sapiens
<220> FEATURE:
<221> NAME/KEY: misc_feature
<222> LOCATION: (1)..(330)
<223> OTHER INFORMATION: Human antibody

<400> SEQUENCE: 50
cagtctccag ccaccctgtc tttgtctcca ggggaaagag ccaccctctc ctgcagggcc      60
agtcagagtg ttagcagcta cttagcctgg taccaacaga aacctggcca ggctcccagg     120
ctcctcatct atgatgcatc caacagggcc actggcatcc cagccacctt cagtggcagt     180
gggtctggga cagacttcac tctcaccatc agcagcctag agcctgaaga ttttgcagtt     240
tattactgtc agcagcgtag caactgggtc tcactttcg gcggagggac caaggtggag      300
atcaaacgaa ctgtggctgc accatctgtc                                      330

<210> SEQ ID NO 51
<211> LENGTH: 312
<212> TYPE: DNA
<213> ORGANISM: Homo sapiens
<220> FEATURE:
<221> NAME/KEY: misc_feature
<222> LOCATION: (1)..(312)
<223> OTHER INFORMATION: Human antibody

<400> SEQUENCE: 51
ggtcctgtct caggtgcagc tgcaggcagt cgggcccagt gactggtgaa gccttcggag      60
accctgtccc tcacctgcac tgtctctggt ggctccatca gcagtagtag ttactactgg     120
ggctggatcc gccagccccc agggaagggg ctggagtgga ttgggagtat ctattatagt     180
gggagcacct actacaaccc gtccctcaag agtcgagtca ccatatccgt agacacgtcc     240
aagaaccagt tctccctgaa gctgagctct gtgaccgccg cagacacggc tgtgtattac     300
tgtgcgagac ag                                                         312

<210> SEQ ID NO 52
<211> LENGTH: 310
<212> TYPE: DNA
<213> ORGANISM: Homo sapiens
<220> FEATURE:
<221> NAME/KEY: misc_feature
<222> LOCATION: (1)..(310)
<223> OTHER INFORMATION: Human antibody

<400> SEQUENCE: 52
ggtcctgtcc cagctgcagc tgcaggagtc gggcccagga ctggtgaagc cttcggagac      60
cctgtccctc acctgcactg tctctggtgg ctccatcagc agtagtagtt actactgggg     120
ctggatccgc cagcccccag ggaaggggct ggagtggatt gggagtatct attatagtgg     180
```

-continued

```
gagcacctac tacaacccgt ccctcaagag tcgagtcacc atatccgtag acacgtccaa        240
gaaccagttc tccctgaagc tgagctctgt gaccgccgca gacacggctg tgtattactg        300
tgcgagacag                                                               310
```